US008209044B2

(12) United States Patent
Inoue

(10) Patent No.: US 8,209,044 B2
(45) Date of Patent: Jun. 26, 2012

(54) MODELING DATA CREATING SYSTEM, MANUFACTURING METHOD, AND MODELING DATA CREATING PROGRAM

(75) Inventor: Tomoyuki Inoue, Kyoto (JP)

(73) Assignee: Shofu, Inc., Kyoto-shi (JP)

( * ) Notice: Subject to any disclaimer, the term of this patent is extended or adjusted under 35 U.S.C. 154(b) by 338 days.

(21) Appl. No.: 12/444,942

(22) PCT Filed: Oct. 10, 2007

(86) PCT No.: PCT/JP2007/069723
§ 371 (c)(1),
(2), (4) Date: Apr. 9, 2009

(87) PCT Pub. No.: WO2008/044693
PCT Pub. Date: Apr. 17, 2008

(65) Prior Publication Data
US 2010/0042241 A1 Feb. 18, 2010

(30) Foreign Application Priority Data
Oct. 10, 2006 (JP) .................................. 2006-276201

(51) Int. Cl.
G06F 19/00 (2006.01)
(52) U.S. Cl. .......................................... 700/98; 700/117
(58) Field of Classification Search ............... 700/95–98
See application file for complete search history.

(56) References Cited

U.S. PATENT DOCUMENTS

| 5,691,905 A | * | 11/1997 | Dehoff et al. .................. 700/98 |
| 5,880,962 A | * | 3/1999 | Andersson et al. ............. 700/98 |
| 6,463,344 B1 | * | 10/2002 | Pavloskaia et al. ............. 700/98 |
| 6,633,789 B1 | * | 10/2003 | Nikolskiy et al. ............... 700/98 |
| 6,665,570 B2 | * | 12/2003 | Pavloskaia et al. ............. 700/98 |
| 6,682,684 B1 | | 1/2004 | Jamalabad et al. |
| 6,772,026 B2 | * | 8/2004 | Bradbury et al. ............... 700/98 |

(Continued)

FOREIGN PATENT DOCUMENTS

JP 2001-277369 10/2001

(Continued)

OTHER PUBLICATIONS

Paul F. Jacobs et al., "Fundamentals of Stereolithography", *Rapid Prototyping & Manufacturing*.

(Continued)

Primary Examiner — Albert Decady
Assistant Examiner — Anthony Whittington
(74) *Attorney, Agent, or Firm* — Stein McEwen, LLP

(57) ABSTRACT

A modeling data creating system comprises: a correction unit that corrects structure data expressing the form of a desired structure based on change amount data; a contour generation unit that generates contour data expressing the contour of a support member for supporting the structure on a modeling table, based on the structure data; a support member generation unit that generates support member data expressing the form of multiple column bodies within the contour expressed by the contour data; and a cross-section generation unit that generates cross-sectional data expressing the cross-sectional shape of each of multiple planes approximately parallel to the modeling table, the planes making up a model configured of the support member expressed by the support member data and the structure expressed by the structure data. Through this, the modeling data creating system suppresses a difference in the model that is to be formed and the modeling data expressing the form of the model.

18 Claims, 22 Drawing Sheets

U.S. PATENT DOCUMENTS

| | | | |
|---|---|---|---|
| 6,882,894 B2* | 4/2005 | Durbin et al. | 700/118 |
| 7,013,191 B2* | 3/2006 | Rubbert et al. | 700/98 |
| 7,092,780 B2* | 8/2006 | Ganley et al. | 700/117 |
| 7,228,191 B2* | 6/2007 | Hofmeister et al. | 700/98 |
| 7,236,842 B2* | 6/2007 | Kopelman et al. | 700/98 |
| 7,245,977 B1* | 7/2007 | Simkins | 700/98 |
| 7,328,077 B2* | 2/2008 | Durbin et al. | 700/98 |
| 7,333,874 B2* | 2/2008 | Taub et al. | 700/117 |
| 7,383,094 B2* | 6/2008 | Kopelman et al. | 700/118 |
| 7,463,942 B2* | 12/2008 | O'Brien et al. | 700/118 |
| 7,474,932 B2* | 1/2009 | Geng | 700/98 |
| 7,774,080 B2* | 8/2010 | Holzner et al. | 700/97 |
| 7,844,429 B2* | 11/2010 | Matov et al. | 703/7 |
| 2002/0025503 A1* | 2/2002 | Chapoulaud et al. | 433/24 |
| 2004/0096799 A1* | 5/2004 | Hughes et al. | 433/24 |
| 2004/0133293 A1* | 7/2004 | Durbin et al. | 700/98 |
| 2004/0220691 A1* | 11/2004 | Hofmeister et al. | 700/98 |
| 2005/0043835 A1* | 2/2005 | Christensen | 700/98 |
| 2006/0079981 A1* | 4/2006 | Rubbert et al. | 700/98 |
| 2006/0122719 A1* | 6/2006 | Kopelman et al. | 700/98 |

FOREIGN PATENT DOCUMENTS

| | | |
|---|---|---|
| JP | 22001-277369 | 10/2001 |
| JP | 2002-166481 | 6/2002 |
| JP | 2004-508222 | 3/2004 |
| JP | 2004-344623 | 12/2004 |
| JP | 2005-059477 | 3/2005 |
| JP | 2007-062050 | 3/2007 |
| WO | WO 02/20251 | 3/2002 |

OTHER PUBLICATIONS

Takeo Nakagawa et al., "Layer Stepped System".
Yoji Maruya et al., "Stereolithography".
Paul F. Jacobs, Ph.D., "Fundamentals of Stereo Lithography", *Rapid Prototyping & Manufacturing*, 1992, pp. 185-187 and 277-285.
Partial Translation of Takeo Nakagawa et al., "Layer Stepped System: New Development in 3D Copy Technology", Kogyo Chosakai Publishing Co., Ltd., Nov. 15, 1996, p. 20, pp. 38-40 and pp. 142-146.
Japanese Office Action dated Apr. 5, 2011, issued in corresponding Japanese Patent Application No. 2008-538732.

* cited by examiner

MODELING DATA CREATING SYSTEM, MANUFACTURING METHOD, AND MODELING DATA CREATING PROGRAM

CROSS-REFERENCE TO RELATED APPLICATIONS

This application claims the benefit of PCT International Patent Application No. PCT/JP2007/069723, filed Oct. 10, 2007, and Japanese Patent Application No. 2006-276201, filed Oct. 10, 2006, in the Japanese Patent Office, the disclosures of which are incorporated herein by reference.

BACKGROUND OF THE INVENTION

1. Field of the Invention

The present invention relates to a modeling data creating system that creates data used by a layered modeling apparatus that forms a model by layering modeling layers, parts of which have been selectively shaped, on a base plane.

2. Description of the Related Art

With prostheses such as crowns, bridges, inlays, onlays, or implants used in prosthetic treatments for the purpose of restoring facial, masticatory, pronunciation, or vocalization functionality to patients, there is a demand for the devices to maintain a high degree of strength and durability within the oral cavity for a long period of time. In addition to restoring lost functionality, aesthetic qualities have also come into higher demand in recent years.

Conventionally-used manufacturing methods, which primarily involve manual work on the part of a dental technician, have been insufficient in meeting this increased demand. A high degree of expertise is required when manufacturing prostheses by hand. There is also a wide range of compatibility, functionality, and durability depending on the manual work performed. Furthermore, there is also the possibility for a large degree of variance even among prostheses created by the same worker. There has thus been significant instability with respect to quality.

In addition, when manufacturing prostheses, dental technicians must perform operations involving many steps while using an extremely wide variety of materials, and thus a wide range of materials, clinical knowledge, and extensive experience are necessary. Therefore, the dental technicians must endure long hours of work, which poses a significant burden to them. Furthermore, as a result of such conditions, the production costs of such prostheses have been climbing as well.

Meanwhile, various improvements are being made to materials to respond to the demand for increased physical properties, and new materials hitherto unused are coming into practical use. For example, porcelain fused to metal restoration, in which ceramics matching the color of natural teeth are baked onto the surface of a metallic frame, have conventionally been the mainstream. However, recent years have seen an increase in the manufacture of all-ceramic crowns in which the entire prosthesis, including the frame, is formed of ceramics, the manufacture of frames using aluminum, zirconia, or the like to provide a strength equal to or comparable to that of a metallic frame while also providing aesthetic qualities superior to metallic frames, and so on, with the goal of eliminating the metallic color from such frames.

Among these materials, items that are difficult to process by hand, whose manufacturing processes are extremely complicated or require long periods of time, or the like are not uncommon. The result is that the dental technician is required to have knowledge regarding these new materials, and have acquired or have experience with processing techniques, leading to an even larger burden.

In addition, procedures for correcting shrinkage of the prosthesis due to firing are more complicated than with conventional devices, and cases in which the manufacture of prostheses with a high compatibility is difficult are more common. This not only increases the burden on the dental technician, but also makes it difficult to satisfy the patient.

Prostheses manufactured in this manner, by a dental technician performing complicated and high-level procedures over a long span of time, thus have a limit in terms of output due to such manual manufacturing procedures. In light of an increase in demand for prosthesis due to recent trends toward an aging society and an increase in tooth loss due to periodontal diseases, it is currently difficult to maintain a sufficient supply of prostheses that have a certain level of quality.

In order to ameliorate such problems with conventional prosthesis manufacturing processes that rely mainly on manual work performed by a dental technician, many methods that attempt to improve the quality and increase the manufacturing efficiency of structural materials having complex structures by applying computer processing techniques, which have seen marked progress recently, have been developed.

For example, CAD/CAM cutout systems, which have been common in dentistry prior to the layered modeling method, use a method in which when manufacturing a frame by cutting a material with high physical properties, such as zirconia, a semi-sintered block material is first cut out and formed into shape before the final sintering. With this method, there is a significant loss of materials due to the occurrence of cut debris resulting from the cutting system. Moreover, in some cases, there are constraints on the shapes that can be processed; for example, an undercut shape cannot be processed.

However, correcting distortions caused by such shape constraints to maintain the compatibility ultimately requires the shape to be adjusted to the actual teeth, which involves long hours of manual labor. Also, because materials such as zirconia have high physical properties, they are difficult to cut with normal dental cutting tools, which makes it necessary to consume a large amount of cutting materials, leading to a rise in manufacturing costs. Furthermore, there have also been cases where the merits of production improvements and quality assurance resulting from mechanization, which solved problems with manual labor such as gaps in compatibility and finishing, were lost.

With a CAD/CAM cutout system that employs a method of cutting a block that has undergone a final sintering, the finishing operations are performed by a machine rather than a dental technician, meaning that the finish, compatibility, and so on tend to be stable, regardless of whether the level of the finish, compatibility, and so on is actually sufficient. However, in the case where, for example, zirconia is being cut, a high-physical property zirconia block is being cut from the first rough-cut step to the final finishing step, and thus the number of cutting tools that are consumed increases, as does the time for cutting. For this reason, the amount of energy consumed in order to run the device increases, resulting in an overall increase in the manufacturing cost.

In order to eliminate such problems with a dental CAD/CAM cutout system, a layered modeling apparatus that, for example, creates a desired model by layering a powder upon a modeling table in layers has been proposed (see, for example, Patent Documents 1 and 2).

FIG. 20 is a diagram illustrating a process by which the stated layered modeling apparatus forms a model. First, as shown in FIG. 20A, a powder is evenly distributed by a powder feeder 42 upon a modeling table 41 provided in the layered modeling apparatus, thereby forming a powder layer 51. Next, as shown in FIG. 20B, an inkjet head 43 ejects a solution onto an area 51a of the powder layer 51, the area 51a representing an area to be modeled. The area 51a, onto which the solution was ejected, is shaped by, for example, irradiation with light. The operations in FIGS. 20A and 20B are then repeated each time the modeling table 41 descends by a predetermined pitch. As a result, multiple powder layers, parts of each being selectively shaped, are layered upon one another, as shown in FIG. 20C. When the powder that has not been shaped is removed at the end, only the shaped portions remain as the model (see FIG. 20D). Using such a layered modeling apparatus makes it possible to form a structural material having a complex shape, such as a structural material used for dental purposes.

After this, the model is sintered and then run through a finishing process, thus completing the desired structure.

Patent Document 1: JP 2004-344623A
Patent Document 2: JP 2005-59477A

SUMMARY OF THE INVENTION

However, when a model formed by the abovementioned layered modeling apparatus is applied to the frame of a prosthesis or the like, it is necessary to perform a sintering process following the modeling, and there have thus been many situations where the model sags or collapses under its own weight or due to the atmosphere within the kiln as the temperature rises, thereby taking on a different shape than was originally intended. In particular, when firing a long model, such as a long-span bridge frame, distortions often occur to a degree that cannot be corrected. Meanwhile, even if a model is formed from a material that does not require firing, there are cases where the model distorts due to drying during shaping, polymerization, and so on.

In addition, because frames for dental prostheses and the like are often designed to be applied and luted to the patient's anchor teeth using a material such as a cement, there are many situations where there is space between the frame and the modeling table. For this reason, it is easy for deformations that cannot be predicted in advance to occur.

Accordingly, it is an object of the present invention to provide a modeling data creating system and program for creating modeling data expressing a model having a structure resistant to deformations during the forming process or the firing process, as well as a manufacturing method for such a model.

A modeling data creating system that creates modeling data expressing the form of a structure, the modeling data being used by a layered modeling apparatus that layers, upon a base plane, modeling layers that have been at least partially shaped through light irradiation or saturation of a binder liquid, the shaped parts forming the model, and the system including: a structure data input unit that inputs structure data expressing the form of a desired structure; a composition data recording unit that records composition data expressing the composition of a material used in the model formed by the layered modeling apparatus; a change amount data recording unit that records a composition of a material that may be used in the model in association with change amount data indicating the amount of change that material will undergo due to drying, polymerization, or sintering; a correction unit that obtains the change amount data indicating the amount of change corresponding to the composition of the material indicated in the composition data from the change amount data, and based on the obtained change amount data, corrects the structure data so that the model formed using the structure data resembles the form of the desired structure after the change caused by drying, polymerization, or sintering; a contour generation unit that uses the structure data to generate contour data expressing the contour of a space between the structure and a projection plane in which the structure is positioned above the base plane and the positioned structure is projected vertically onto the base plane; a support member generation unit that generates support member data expressing the form of a support member that is formed so as to approximately fill the entirety of the space and support the structure; and a cross-section generation unit that generates cross-sectional data expressing the cross-sectional shape of each of multiple planes approximately parallel to the base plane, based on the structure data, the support member data, and the contour data.

By using change amount data indicating the amount of change caused by drying, polymerization, or sintering of the model, the correction unit can correct structure data in accordance with the amount of change such as shrinkage and distortion due to the drying, polymerization, and sintering, predicted in advance. The structure data is therefore corrected so that the model formed by the layered modeling apparatus based on the structure data is as close as possible to the desired form. Through this, structure data that achieves the target form and size following the drying, polymerization, or sintering (firing) of the model is obtained.

Furthermore, the support member generation unit generates the support member data expressing the form of a support member that is formed so as to approximately fill the entirety of the space expressed by the contour data. For this reason, the model configured by the support member expressed by the support member data and the structure expressed by the structure data is configured so that the surface of the side of the base plane of the structure, or in other words, the bottom surface of the structure, is supported approximately in its entirety above the base plane by the support member.

Cross-sectional data, expressing the cross-sectional form of the model, is generated using the corrected structure data, the support member data, and the contour data. As mentioned above, the layered modeling apparatus uses this cross-sectional data, whereby the correction unit corrects the structure data having anticipated the amount of change occurring due to the forming and firing processes for the model. As a result, the model that has been layered using the cross-sectional data and sintered takes on a form that accurately reflects the desired structure form expressed by the structure data inputted through the structure data input unit. That is, a decrease in compatibility, precision, and so on due to changes such as shrinkage of the structure occurring during the processes for forming or sintering the structure expressed by the structure data is suppressed.

Furthermore, the structure layered using the cross-sectional data is formed upon the bottom surface of the base plane so as to be supported approximately in its entirety by the support member. For this reason, distortions in the structure such as bowing are suppressed in the process of forming the model based on the cross-sectional data. Moreover, in the formation process, the bottom surface of the structure is supported in its entirety by the support member, and thus the structure is accurately formed while its target form is maintained.

Therefore, the modeling data creating system can provide modeling data for obtaining a model that resists distortion during the forming process and accurately reflects a desired form following the formation and sintering processes. This modeling data creating system can provide modeling data that is useful in the modeling of structures that have complex surfaces and require precise forming, such as crowns, bridges, and the like.

According to the present invention, the present invention can provide a modeling data creating system and program for creating modeling data expressing a model having a structure resistant to deformations during the forming process or the sintering process, as well as a manufacturing method for such a model.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 9 is a diagram illustrating an example of a screen that displays a state in which the contour 33 has been superimposed upon the column bodies 34a;

FIG. 10 is an example of a screen that displays the form of a support member 34 formed by trimmed column bodies 34a;

DETAILED DESCRIPTION OF THE EMBODIMENTS

Figure 1:
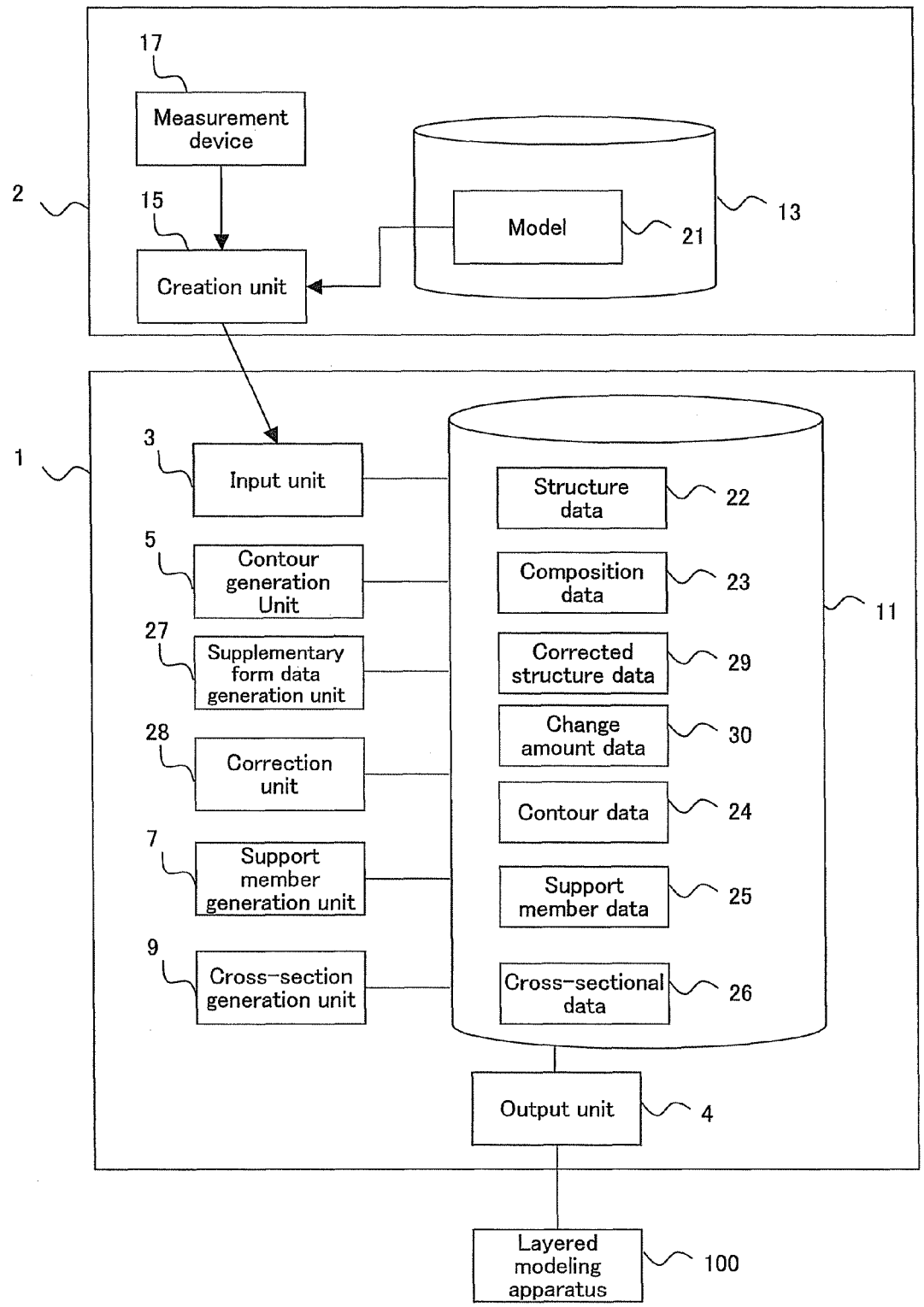
FIG. 1 is a functional block diagram illustrating the configuration of a modeling data creating system according to Embodiment 1.

According to an aspect of the present invention, in the case where the desired structure is to be attached to another object, the structure data input unit can further input relationship data indicating the relative positional relationship between the object and the structure; and the system can further include a supplementary form data generation unit that generates supplementary form data expressing a member for fixing the positional relationship between the object and the structure based on the relationship data, and adds the supplementary form data to the structure data.

The supplementary form data generation unit generates structure data to which has been added information expressing a member for fixing the positional relationship between the structure and the object to which the structure is to be attached. When cross-sectional data generated from this structure data is used by the layered modeling apparatus, a structure to which the member has been added is formed. In other words, structure data expressing a structure whose orientation, position, and so on can be determined uniquely, and which can be precisely applied when attaching the structure to an object, is obtained. As a result, the structure can be attached to the object in the correct position and with the correct orientation. Skew in the orientation when the structure is attached to the object is also suppressed.

For example, in the case where the structure to be modeled is to be used as a frame such as a crown or a bridge, the supplementary form data generation unit makes it possible to add a cement space for luting or adhering to an anchor tooth, to position the frame so as to maintain the proper position and orientation of the frame relative to the anchor tooth, and so on.

According to an aspect of the present invention, the supplementary form data generation unit can generate data expressing plate bodies or column bodies provided between the object and the structure as the supplementary form data, and generates the supplementary form data by finding the cross-sectional surface area of the plate bodies or column bodies using the composition data recorded in the composition data recording unit.

Because the member expressed by the supplementary form data represents multiple plate bodies or column bodies, the space between the structure expressed by the cross-sectional data and the object is supported by the member at multiple locations, and the surface area over which the structure and the member make contact is reduced. Through this, it is easy to accurately position a structure having a precise shape relative to the object.

According to an aspect of the present invention, the supplementary form data generation unit can generate the supplementary form data by calculating, using the structure data and the relationship data, the surface area of the portion where the member makes contact with the object so that the surface area is sufficient for fixing the positional relationship and sufficient for keeping the adhesive strength between the structure and the object above a predetermined value.

Through this, supplementary form data that enables the relative positions of the structure and the object to be fixed with sufficient strength as well as the structure and the object to be adhered to one another with sufficient strength is obtained.

According to an aspect of the present invention, the supplementary form data generation unit can generate supplementary form data expressing a member, formed from multiple plate bodies or column bodies, that is added to the surface of the structure indicated by the structure data that is attached to the object, that has a thickness equivalent to a desired space provided between the structure and the object, and whose surface that makes contact with the object is the same form as the form of the corresponding portion of the object.

Through this, it is possible to more accurately attach and anchor the completed model while maintaining the proper positioning and orientation of the model relative to the object to which the model is to be attached, the appropriate thickness for adhesion and the like, and so on. For example, in the case where the completed model is a prosthesis attached to an anchor tooth within the oral cavity of a patient, that prosthesis can be accurately attached and anchored while maintaining the proper positioning and orientation relative to the anchor tooth, the appropriate thickness of the cement layer, and so on.

According to an aspect of the present invention, the supplementary form data generation unit can generate supplementary form data expressing a member formed from multiple plate bodies or column bodies extending in the normal direction in the portion of the structure that makes contact with the member. Through this, the supplementary form data generation unit can generate the supplementary form data through simple calculations.

According to an aspect of the present invention, the contour generation unit can determine the positioning of the corrected structure based on the volume of a space formed between the corrected structure data corrected by the correction unit and the base plane, and generate contour data expressing the contour of the space formed between the corrected structure data and the base plane.

Through this, the contour generation unit can arrange the structure so that the volume of the space is optimal. For this reason, the contour data expresses the contour of a space that has the optimal volume. The support member generation unit generates the support member data based on such contour data of a space that has the optimal volume. For this reason, support member data expressing a support member that has the optimal volume is obtained. For example, if the volume of the space decreases, the support member formed within that space can be small as well. In other words, the support member expressed by the support member data decreases in size. As a result, the amount of material used in the formation of the support member can be reduced.

According to an aspect of the present invention, the support member data can express a support member formed from multiple plate bodies or column bodies provided vertically relative to the base plane.

The support member expressed by the support member data is made up of multiple plate bodies or column bodies, and therefore the size of the portion of the support member that makes contact with the structure is reduced. Therefore, the structure expressed by the cross-sectional data is supported in its entirety by the support member, and the surface area that makes contact with the support member is reduced. Such a structure, formed based on cross-sectional data, suppresses distortions during the formation process, and furthermore, remnants thereof rarely remain on the structure if the support member is removed. In other words, when the surface area where the support member and the structure make contact with each other is small, the support member can easily be broken off near the base of the structure when the support member is to be removed. As a result, it is easy to perform post-processing for smoothing the surface of the structure after the support member has been removed. In other words, it is easy to obtain a structure having a precise shape. In this manner, by using the stated support member data, the modeling data creating system makes it possible to provide modeling data for obtaining a precise structure with ease.

According to an aspect of the present invention, the support member data can express a support member in which the horizontal thickness of the plate bodies or column bodies is, in the portion that makes contact with the structure, smaller than in the other portions.

Through this, the size of the surface area of the portion of the support member expressed by the support member data that makes contact with the structure is reduced. In other words, the size of the contact point between the support member and the structure is reduced. Accordingly, with a model modeled based on the cross-sectional data, when the support member is to be removed from the structure, the support member can easily be broken off near the portion that makes contact with the structure. As a result, remnants of the support member rarely remain on the structure. In other words, cross-sectional data generated using the support member data expresses a model having a form with which remnants rarely remain on the support member.

According to an aspect of the present invention, the support member generation unit can generate support member data expressing a support member having a notch near the portion that makes contact with the structure. Through this, support member data expressing a form in which remnants of the support member rarely remain on the structure when the support member is removed from the structure is obtained.

According to an aspect of the present invention, the support member generation unit can correct the structure data so that the periphery of the portion of the structure that makes contact with the support member is recessed toward the inner surface of the structure. Through this, structure data expressing a form in which remnants of the support member rarely remain on the structure when the support member is removed from the structure is obtained.

According to an aspect of the present invention, the composition data recording unit can further record composition data expressing the composition of a material used in the support member; and the support member generation unit can find the horizontal thickness of the plate bodies or column bodies using the composition data recorded in the composition data recording unit.

By using the composition data, the support member generation unit ensures that the support member has the necessary strength, and also obtains the minimum thickness. In other words, the support member generation unit enables the support member to have the appropriate strength while also being able to be easily removed from the structure, and can furthermore find a horizontal thickness for the plate bodies or column bodies of a degree whereby parts of the support member do not remain on the surface of the structure after the support member has been removed.

According to an aspect of the present invention, the support member generation unit can calculate a distribution of force exerted on the support member by the structure using the structure data, and can find the horizontal thickness of the plate bodies or column bodies based on the distribution.

The support member generation unit finds the horizontal thickness for the plate bodies or column bodies based on the distribution of force applied to the support member by the structure; this enables the support member to have the strength necessary to suppress distortions in the structure while also being able to be easily removed from the structure, and furthermore makes it possible to find the thickness of a degree whereby parts of the support member do not remain on the surface of the structure after the support member has been removed. Note that the support member generation unit may find the thickness using both the composition data and the stated distribution of force.

According to an aspect of the present invention, the structure can be a prosthesis within the oral cavity, and the structure data can be data generated based on measurement data obtained by measuring the interior of the oral cavity or the periphery thereof.

Structure data expressing a form of a prosthesis within the oral cavity is generated based on measurement data obtained through the measurement, and has been corrected in advance having anticipated the amount of shrinkage due to drying, polymerization, or sintering; this data therefore expresses a prosthesis in a form that fits the form of the oral cavity or the peripheral portions thereof following the sintering.

A manufacturing method for manufacturing the structure using the cross-sectional data created by the modeling data creating system and the layered modeling apparatus is also an aspect of the present invention. This manufacturing method includes: a layer formation step of forming a modeling layer of a predetermined thickness upon a modeling table, provided in the layered modeling apparatus, that is capable of moving up and down; a modeling step of selectively irradiating with light or ejecting a binder liquid onto and saturating at least a portion of the modeling layer, the portion having a form corresponding to a cross-sectional shape expressed by the cross-sectional data, thereby shaping the modeling layer; a descent step of causing the modeling table to descend by an amount equivalent to the predetermined thickness; a layering step of layering modeling layers by sequentially repeating the layer formation step and the shaping step for each of multiple planes expressed by the cross-sectional data; and a removal step of forming the structure in a state in which the structure is supported upon the modeling table by the support member, by removing the portions of the modeling layer layered in the layering step aside from the portions shaped in the shaping step.

According to the above manufacturing method, the layered modeling apparatus repeats the layer formation step, the shaping step, and the lowering step based on the cross-sectional data; as a result, the portions shaped by the shaping step become the structure supported upon the modeling table by the support member. Distortions occurring in the structure during the process of forming the structure can thus be suppressed. Through the removal step, the support form portions formed at the same time as the structure are removed from the modeling layers.

Furthermore, the structure formed by the layered modeling apparatus takes data that has had changes such as distortion and shrinkage due to sintering corrected in advance, and thus the post-sintering structure has the target size, and has favorable compatibility.

A modeling data creating program that causes a computer to execute a process for creating modeling data expressing the form of a structure, the modeling data being used by a layered modeling apparatus that layers, upon a base plane, modeling layers that have been at least partially shaped through light irradiation or saturation of a binder liquid, the shaped parts forming the model, is also an aspect of the present invention. This program causes a computer to execute: a structure data input process of inputting structure data expressing the form of a desired structure; a correction process of accessing a composition data recording unit that records composition data expressing the composition of a material used in the model formed by the layered modeling apparatus and a change amount data recording unit that records a composition of a material that may be used in the model in association with change amount data indicating the amount of change that material will undergo due to drying, polymerization, or sintering, obtaining the change amount data indicating the amount of change corresponding to the composition of the material indicated in the composition data from the change amount data, and based on the obtained change amount data, correcting the structure data so that the model formed using the structure data resembles the form of the desired structure after the change caused by drying, polymerization, or sintering; a contour generation process of using the structure data to generate contour data expressing the contour of the space between the structure and a projection plane in which the structure is positioned above the base plane and the positioned structure is projected vertically onto the base plane; a support member generation process of generating support member data expressing the form of a support member that is formed so as to approximately fill the entirety of the space and support the structure; and a cross-section generation process of generating, based on the structure data, the support member data, and the contour data, cross-sectional data expressing the cross-sectional shape of each of multiple planes approximately parallel to the base plane, the planes making up the model configured of the support member expressed by the support member data and the structure expressed by the structure data corrected by the correction unit.

According to the above program, the layered modeling apparatus generates support member data used in the creation of the support member for supporting the structure upon the base plane. Furthermore, cross-sectional data, which can be used by the layered modeling apparatus with ease, is generated.

A manufacturing method according to an aspect of the present invention is a model manufacturing method that layers, on a base plane, modeling layers in which parts of the layers are selectively shaped, and forms the parts that have been shaped as a model. The method includes a step of forming a support member for supporting a structure having a desired shape upon the base plane; and a step of forming the structure upon the support member.

Hereinafter, embodiments of the present invention shall be described in detail with reference to the drawings.

Embodiment 1

Embodiment 1 relates to a modeling data creating system that creates data expressing the form of a model formed by layering a powder upon a modeling table. The present embodiment describes an example where a layered modeling apparatus manufactures, for example, a zirconia structure, used as a bridge frame for a porcelain fused to metal restoration, as a model. FIG. 1 is a functional block diagram illustrating the configuration of the modeling data creating system according to Embodiment 1.

As shown in FIG. 1, a modeling data creating system 1 includes an input unit 3, an output unit 4, a supplementary form data generation unit 27, a correction unit 28, a contour generation unit 5, a support member generation unit 7, a cross-section generation unit 9, and a recording unit 11. The modeling data creating system 1 is connected to a prosthesis form data creation system 2 and a layered modeling apparatus 100.

The prosthesis form data creation system 2 includes a measuring device 17, a creation unit 15, and a model recording unit 13. The measuring device 17 measures, for example, the form of the interior of a patient's oral cavity, the peripheral portion thereof, and so on. The form measured by the measuring device 17 is sent to the creation unit 15 as measurement data. The creation unit 15 creates structure data 22 expressing a desired prosthesis form, based on the measurement data sent from the measuring device 17 and a model 21 recorded in the model recording unit 13 in advance. The model 21 includes, for example, data and the like expressing a basic or general structure of a prosthesis.

The input unit 3 loads the structure data created by the creation unit 15 and records that data in the recording unit 11. As a result, the modeling data creating system 1 enters a state in which it can use the structure data 22. In addition, in the case where the structure indicated by the structure data is a structure that is to be attached to another object, the input unit 3 also inputs relationship data indicating the positional relationship between the structure and the object when the attachment has taken place. This relationship data includes, for example, data that specifies the surface of the structure that is to be adhered to the object when the structure is attached to the object, data that indicates the thickness of a space to be provided between the object and the structure, data expressing the form of the object to which the structure is to be attached, and so on.

The supplementary form data generation unit 27 generates supplementary form data based on the structure data 22 recorded in the recording unit 11 and the relationship data, adds this to the structure data, and records the resultant as new structure data 22 within the recording unit 11. The supplementary form data is data expressing the form of a supplementary member (called "supplementary form" hereinafter) that fixes the positional relationship between the structure and the object when the structure expressed by the structure data 22 is attached to the object.

For example, in the case where the structure is a fired ceramic bridge frame (called simply a "frame" hereinafter), supplementary form data is generated expressing the form of a supplementary member for attaching the frame to an anchor tooth within the oral cavity of a patient so that the frame is properly positioned and has the proper orientation with respect to the anchor tooth and is attached while maintaining an appropriate amount of space between the anchor tooth and the frame.

It is preferable for the supplementary form data generation unit 27 to refer to composition data 23 recorded in the recording unit 11 in advance when determining the supplementary form. The composition data 23 is data expressing the composition of the material used to form, for example, the supplementary member, the structure, or the support member.

Note that in the case where the supplementary form is not necessary due to the target usage of the structure that is being manufactured, the supplementary form data generation unit 27 can be skipped.

The correction unit 28 generates corrected structure data 29, in which the structure data has been corrected, based on the structure data 22, composition data 23, and change amount data 30 recorded in the recording unit 11, in order to suppress a reduction in precision and compatibility due to shrinkage and distortion occurring during the drying, polymerization, sintering, and firing of the modeled structure in the subsequent processes. The generated corrected structure data 29 is recorded in the recording unit 11.

The contour generation unit 5 generates contour data 24 based on the corrected structure data 29 recorded in the recording unit 11. The contour data 24 is contour data 24 expressing the contour of a space arising between the structure and the modeling table in the case where the structure expressed by the corrected structure data 29 is disposed upon a base plane, such as, for example, a modeling table. The generated contour data 24 is recorded in the recording unit 11.

The support member generation unit 7 generates support member data 25 expressing the form of a support member that supports the structure upon the modeling table, based on the contour data 24 recorded in the recording unit 11. The support member data 25 is, for example, data expressing the form of a support member provided within the space expressed by the contour data 24. It is preferable for the support member generation unit 7 to refer to composition data 23 recorded in the recording unit 11 in advance when determining the form of the support member. The generated support member data 25 is recorded in the recording unit 11.

The cross-section generation unit 9 generates cross-sectional data 26 based on the corrected structure data 29 and the support member data 25. The generated cross-sectional data 26 is recorded in the recording unit 11.

The output unit 4 outputs the cross-sectional data 26 to the layered modeling apparatus 100. The output unit 4 also outputs a control program for controlling the operation of the layered modeling apparatus 100 to the layered modeling apparatus 100. An example of the control program shall be described later in Embodiment 2. The layered modeling apparatus 100 manufactures a model configured from a support member and a structure based on the cross-sectional data 26 and the control program. The configuration and operations of the layered modeling apparatus 100 shall be described in detail later.

The modeling data creating system 1 and the prosthesis form data creation system 2 are implemented on a computer such as a personal computer, a server, or the like. The modeling data creating system 1 and the prosthesis form data creation system 2 may be implemented on a single computer, or may be separately implemented on two different computers. The functions of the input unit 3, the output unit 4, the contour generation unit 5, the support member generation unit 7, the cross-section generation unit 9, and the creation unit 15 are realized by the CPU of the computer executing predetermined programs. A storage medium such as a hard disk or a RAM installed within the computer, a portable storage medium such as a flexible disk or a memory card, a storage medium within a storage device located on a network, or the like may be used as the recording unit 11 and the model recording unit 13.

Next, operations performed by the modeling data creating system 1 shall be described. The present embodiment describes an example of a process for creating modeling data for a layered modeling apparatus to manufacture a zirconia structure employed as a bridge frame for a porcelain fused to metal restoration to be used by a patient. Here, modeling data is data expressing the form of the model to be manufactured by the layered modeling apparatus.

Figure 2:
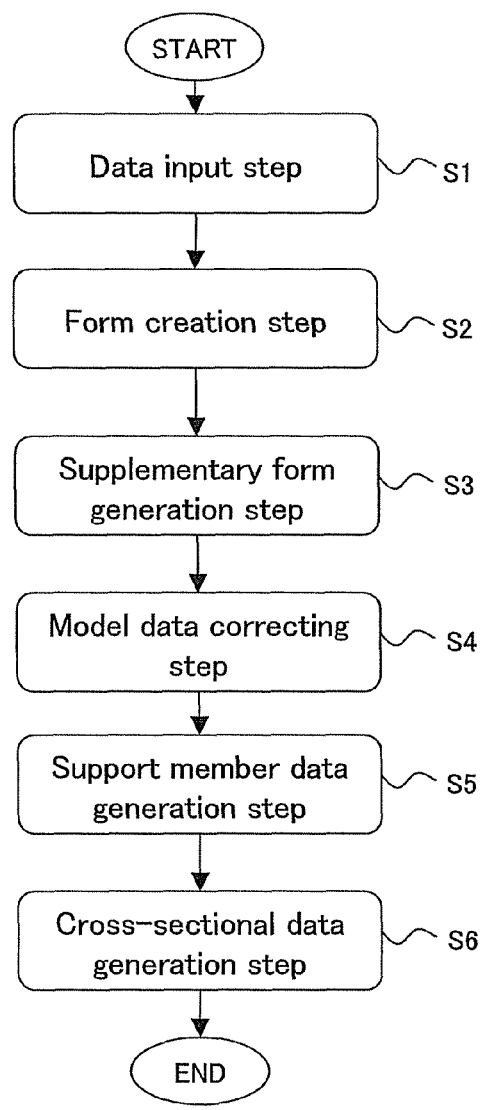
FIG. 2 is a flowchart illustrating the flow of processing when creating modeling data.

First, the overall flow of the process shall be described. FIG. 2 is a flowchart illustrating the flow of processing when the modeling data creating system 1 creates modeling data. As shown in FIG. 2, first, the measuring device 17 of the prosthesis form data creation system 2 measures the oral cavity or the periphery thereof of a patient, thereby obtaining measurement data. The creation unit 15 is inputted with the measurement data from the measuring device 17 (step S1).

The creation unit 15 then creates structure data 22 expressing the form of the target structure, or in other words, the frame, based on the model 21 recorded in the model recording unit 13 and the measurement data. The creation unit 15 also creates relationship data specifying the positional relationship between the frame and the anchor tooth when the frame is attached to the anchor tooth (step S2). The structure data and relationship data created by the creation unit 15 is loaded into the modeling data creating system 1 via the input unit 3 and recorded in the recording unit 11.

The supplementary form data generation unit 27 creates supplementary form data expressing the form of a supplementary member for fixing the position of the frame and the anchor tooth to which the frame is to be attached, using the structure data 22 and the relationship data created by the creation unit 15, and adds this data to the structure data 22 (step S3). Here, the supplementary form is, for example, a positioning guide form for enabling a technician to easily attach the frame at the proper position and orientation when attaching the frame to the anchor tooth of the patient, and/or a spacer form for maintaining a space to be filled with dental cement used for luting or adhesion when attaching the frame to the anchor tooth.

Note that in the case where the supplementary member is not needed, such as a case where the structure is not to be attached to another object, the supplementary form data generation unit 27 does not need to execute the process of the abovementioned step 3.

The correction unit 28 creates corrected structure data 29, in which the structure data 22 created by the creation unit 15 or the supplementary form data generation unit 27 is corrected (step S4). The correction unit 28 corrects the structure data 22 so that differences between the structure indicated by the structure data 22 and the structure that has changed due to shrinkage and distortion occurring when the structure modeled using the structure data 22 is sintered are eliminated, thereby creating the corrected structure data 29.

In step S4, the correction unit 28 refers to or calculates a shrinkage amount of the model using the composition data 23 and the change amount data 30 recorded in the recording unit 11, performs the necessary corrections using this shrinkage amount, and generates the corrected structure data.

The contour generation unit 5 and the support member generation unit 7 use the corrected structure data 29 created by the correction unit 28 to create support member data 25 expressing the form of a support member that supports the structure (step S5).

The cross-section generation unit 9 generates the cross-sectional data 26 expressing cross-sectional forms of the model configured by the support member and the corrected structure, the forms being multiple planes of the model that are parallel to one another (step S6). In the present embodiment, this cross-sectional data 26 is modeling data for manufacturing the target structure, which is a frame.

Next, the detailed processes of the steps S1 to S6 shall be described, using the case where a bridge frame is the desired structure as an example.

(Step S1 Data Input Process)

In step S1, the measuring device 17 of the prosthesis form data creation system 2 inputs, to the creation unit 15, measurement data obtained by measuring, for example, the oral cavity of a patient who is to use a bridge and the vicinity of the anchor tooth. The measurement data is, for example, values unique to the patient, such as anchor tooth forms, anchor teeth, forms of antagonistic tooth row, occlusal vertical dimensions (upper and lower jaw intervals), centric relation (central positions), Gothic arches, and so on. A "Gothic arch" denotes the movement path of a specific portion arising during movement of the jaw. The oral cavity of the patient and the form of the periphery of the anchor tooth are expressed, for example, as point group data, or in other words, as a collection of XYZ coordinate values.

(Step S2 Form Creation Process)

Figure 3A:
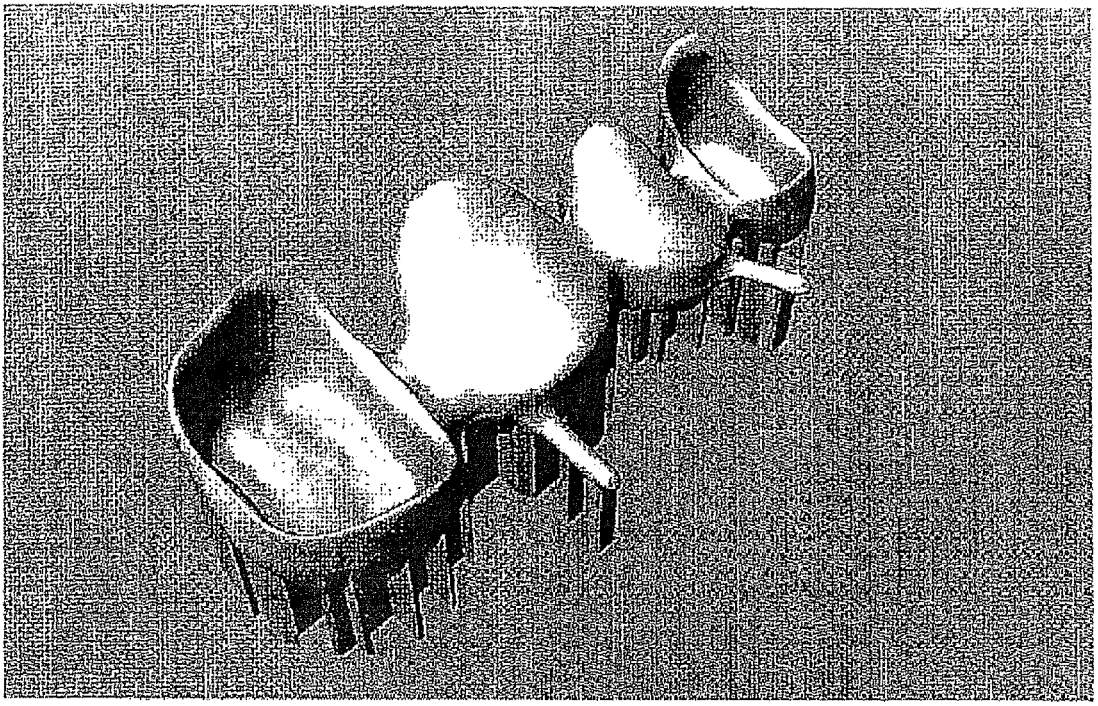
FIG. 3A is a diagram illustrating an example of a bridge frame expressed by corrected structure data 29 created by a correction unit 28.

In the form creation process in step S2, the creation unit 15 creates the structure data 22 and the relationship data based on the model 21 recorded in the model recording unit 13 and the measurement data. FIG. 3A is a diagram illustrating an example of a frame expressed by structure data 22 created by the correction unit 15. Note that FIG. 3A illustrates a state in which the frame is formed upon a support member generated in step S5, described later.

The creation unit 15 determines the general form of the frame to be manufactured, based on data from the measurement data such as the form of the anchor tooth, adjacent teeth, antagonistic teeth (the partner teeth when biting), the dental shape on the opposite side, the occlusal vertical dimensions (interval of the upper and lower jaws), the centric relation (central position), Gothic arches, and so on.

The model 21 recorded in the model recording unit 13 is a model for recreating, for example, a crown, a bridge, or the like. The model 21 includes, for example, databases for crowns for each tooth in each position and various frame forms that make up the base for creating bridge forms composed of various parts and numbers of teeth, models that express basic or general pontic forms, and so on. The creation unit 15 causes a model 21 expressing a general crown and bridge form to reflect the patient-unique values obtained from the stated measurement data, thereby creating a frame model expressing the overall form of the frame.

The creation unit 15 specifies, for example, the material of the frame by referring to the composition data 23, and calculates the minimum necessary frame thickness and so on for achieving the necessary strength from the specified frame material. In addition, the creation unit 15 obtains information of cement spaces suited to the frame material or the like from, for example, pre-recorded data. The creation unit 15 can furthermore determine the form of the base surface of the bridge frame (that is, the surface that adheres to the anchor tooth) based on anchor tooth data by using this cement space information.

Combining the base surface of the bridge frame, the frame thickness, and so on determined in this manner with the stated frame model generates the structure data 22 expressing the form of a frame, such as that shown in FIG. 3A. Meanwhile, the creation unit 15 may record data for specifying the base surface of the frame that adheres to the anchor tooth, data indicating cement spaces, and so on as relationship data.

(Step S3 Supplementary Form Creation Process)

The supplementary form creation process in step S3 is performed in the case where a supplementary form is necessary, such as cases where it is necessary to secure an accurate space, perform positioning, and so on. For example, in the case where the input unit 3 has loaded relationship data in addition to the structure data 22 created by the creation unit 15, the modeling data creating system 1 can determine that the supplementary form creation process is necessary.

In the case where it has been determined that the supplementary form creation process in step S3 is necessary and is to be executed, the supplementary form data generation unit 27 is called. The supplementary form data generation unit 27 uses the structure data 22 created and recorded in the recording unit 11 in the form creation process in step S2 to generate the numerical value features of the supplementary member, and adds the resultant to the structure data 22. A guide form is generated as the numerical value features of the supplementary member, so that, for example, the necessary amount of space between the frame and the anchor tooth, the correct orientation and position of the frame when a space is provided between the anchor tooth and the frame, and so on can be determined.

Through this, the completed structure, or frame, can be attached to the anchor tooth in the proper position with the proper orientation, and it is also possible to secure the necessary amount of cement space, thereby realizing reliable luting or adhesion to the anchor tooth.

At least three supplementary forms for positioning are configured. In addition, the surfaces of the supplementary forms that come into contact with the anchor tooth are required to at least be of a size that provides the supplementary form with a sufficient degree of strength. At the same time, the contact surface area of the supplementary forms themselves are required to be as small as possible, so that a surface area that enables dental cements or adhesive materials to come into sufficient contact with the frame and the anchor tooth can be secured without obstructing those materials from sufficiently luting or adhering the anchor tooth to the frame.

In the supplementary form generation process in step S3, the supplementary form data generation unit 27 refers to the structure data 22, the relationship data, and the composition data 23 in order to determine the form and number of supplementary members so as to balance out such conflicting conditions.

Here, a specific example of the supplementary form determination process shall be described. First, the supplementary form data generation unit 27 removes, from the side of the structure data 22 that is to be attached to the anchor tooth, a thickness indicated by the relationship data or of the same amount as a cement space inputted by an operator of the system. Through this, a desired space is provided between the surface of the side of frame, indicated by the original structure data 22, that is to be attached to the anchor tooth, or in other words, the base surface of the frame, and the anchor tooth.

Next, the supplementary form data generation unit 27 generates supplementary form data indicating the form of the supplementary member to be provided in the stated space. For example, data expressing plate bodies or column bodies extending in the normal direction from the frame within the stated space is generated as the supplementary form data (hereinafter, the case where the supplementary member is column bodies shall be described as an example). A similar method to that used by the support member generation unit 7 to generate the data expressing the column bodies (step S5), which shall be described later, can also be used to generate this data expressing column bodies within the predetermined space. Furthermore, for example, the form surface of the anchor tooth may be offset as-is in the direction of the frame, and data expressing column bodies extending in the normal direction from the frame may be calculated. Next, the supplementary form data generation unit 27 calculates the cross-sectional surface area of the column bodies, or in other words, the area of the surface of the supplementary member that makes contact with the anchor tooth. Each of the surfaces of the supplementary members that make contact with the anchor tooth is required to be of at least a size whereby the supplementary member has a strength sufficient for positioning the frame and anchor tooth. If the surface area of the portions where the anchor tooth and the supplementary member make contact are extremely small when the frame is attached, the stress placed on the anchor tooth is concentrated in that small range, and thus there is the possibility that the anchor tooth will be damaged. Therefore, the cross-sectional surface area of the column bodies is required to be set to be sufficiently large in order to fix the position of the anchor tooth and the frame.

Meanwhile, it is necessary that adhesive materials such as dental cements or bonding materials are not obstructed from sufficiently luting or adhering the anchor tooth and the frame. Therefore, it is necessary to secure a surface area that allows this adhesive material to come into sufficient contact with the frame and the anchor tooth. For this reason, if the portion of the supplementary member that makes contact with the anchor tooth is too large, excessive adhesive material remains between the supplementary member and the anchor tooth when the frame is attached to the anchor tooth, the frame may be fixed with a greater thickness than was set. In order to prevent such an occurrence, the surface area of the supplementary member that makes contact with the anchor tooth, or in other words, the cross-sectional surface area of the column bodies, is required to be as small as possible.

The supplementary form data generation unit generates supplementary form data that fulfils the stated two conflicting conditions, referring to the composition data 23. First, an example in which the cross-sectional surface area of the column bodies is calculated so that the supplementary member has at least the strength sufficient to position the frame and the anchor tooth shall be described. For example, the supplementary form data generation unit 27 refers to the relationships between cross-sectional surface areas and strengths recorded in the recording unit 11, which have been calculated in advance for each composition of material used for the supplementary member. This relationship between the cross-sectional surface area and strength can be found by performing strength tests, such as bending strength tests, using, for example, test samples manufactured with various changes to the cross-sectional surface areas of the column bodies created from the material used in the supplementary member. The supplementary form data generation unit 27 finds the necessary strength of the supplementary member having taken into consideration the form and so on of the supplementary member, and performs an inverse operation for finding the cross-sectional surface area necessary to realize the required strength using the relationship between the cross-sectional surface area and the strength.

Next, an example in which the column body cross-sectional surface area necessary for securing a surface area that enables the adhesive material to come into sufficient contact with the frame and the anchor tooth is calculated shall be described. First, the adhesive strength between the adhesive material and the frame per unit of surface area and the adhesive strength between the materials used and the anchor tooth per unit of surface area are obtained and recorded, in advance, into the recording unit 11, as basic data. The adhesive strength is in direct correlation with the rise/fall of the adhesive surface area. For this reason, by calculating the adhesive strength necessary to attach the frame and referring to the stated adhesive strength per unit of surface area, the supplementary form data generation unit 27 can find the adhesive surface area necessary to realize the stated necessary adhesive strength.

Figure 21A:
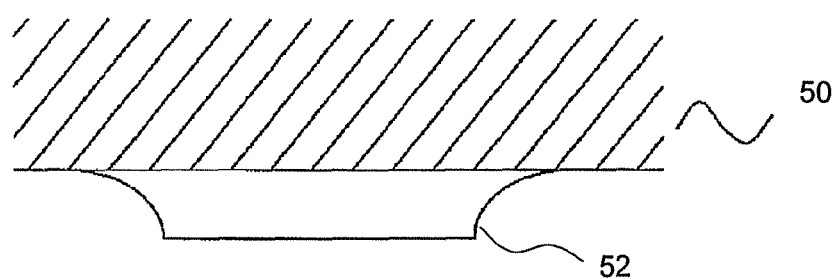
FIG. 21A is a diagram illustrating the cross-section of a supplementary member 52 of a type having a corner on the shoulder of the portion that makes contact with the anchor teeth.
Figure 21B:
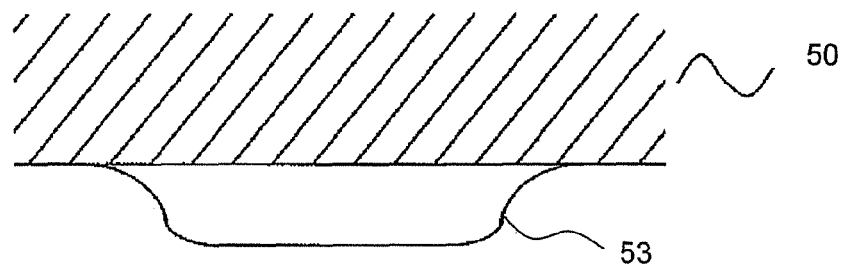
FIG. 21B is a diagram illustrating the cross-section of a supplementary member 53 of a type in which the shoulder of the portion that makes contact with the anchor teeth is rounded.

FIGS. 21A and 21B are cross-sectional views illustrating examples of the form of the supplementary member added to a model (the frame) 50. FIG. 21A is an example of a type having a corner on the shoulder of the portion that makes contact with the anchor tooth. FIG. 21B, meanwhile, is an example of a type in which the portion that makes contact with the anchor tooth is rounded. With a supplementary member of such a type, when frame 50 is attached to an anchor tooth, even when cement is present on the surface of the supplementary member 53 that makes contact with the anchor tooth, the cement can be smoothly removed from the surface of the supplementary member 53 that makes contact with the anchor tooth. This has an effect of reducing residual stress.

In the examples shown in FIGS. 21A and 21B, the configuration that employs a curved surface rather than a corner at the portion where the model 50 connects to the supplementary members 52 and 53 is designed to ensure the strength of the connecting portion. Too large a radius for the curved surface results in the set surface area of the spacer being insufficient, leading to design problems. However, if the radius is too small, the result is essentially the same as when making the connection using corners, which leads to the possibility for it being difficult for the cement to be filled, a drop in strength, the occurrence of cracking, and so on. It is preferable for the radius of the curved surface of the connection portion to be between 0.1 to 3 times the distance between the anchor tooth and the frame.

Of course, the supplementary form is not limited to the form shown in FIGS. 21A and 21B, which spreads out on the side of the model; no particular limitations are made on the form as long as an appropriate cement space can be secured and the model can be attached at the proper orientation and position.

The supplementary member can also take on a form in which multiple long band-shaped members are provided. It is preferable for such a supplementary form to be applied in, for example, a prosthesis installed across a wide area within the patient's oral cavity, such as a stent.

Next, the supplementary form data generation unit 27 finds the number of supplementary members necessary for attaching the frame at the proper orientation and the proper position, and the effective installment positions of those supplementary members. The supplementary form data generation unit 27 determines, based on the form of the frame expressed by the structure data 22, the number and positions so that the direction of the frame is uniquely determined when the frame is attached to the anchor tooth. When the frame is luted to the anchor tooth, the direction of that force is limited, and thus the number and positions of the supplementary members can be determined, to a degree, based on empirical rules.

For example, in the case where the structure is a single crown, at least two supplementary members are used. Although there is no upper limit on the number of supplementary members with a single crown, between three and twelve are preferable. Meanwhile, in the case where the structure is a prosthesis that has multiple anchor tooth attachment areas, such as a bridge, it is desirable to provide the above-mentioned number of pieces of supplementary form data for each anchor tooth attachment area.

As installation areas for the supplementary members in the front teeth, it is preferable, for example, to provide at least one supplementary member in at least one area including the labial surface, lingual surface, mesial surface, and distal surface when viewed from the incisal edge, and in at least one area including the intermediate points thereof, or in other words, in the vicinity of the connection between the lingual surface and the mesial surface, the vicinity of the connection between the mesial surface and the labial surface, the vicinity of the connection between the labial surface and the distal surface, and the vicinity of the connection between the distal surface and the lingual surface.

For molars, it is preferable, for example, to provide at least one supplementary member in at least one area including the buccal surface, lingual surface, mesial surface, and distal surface, and in at least one area including the intermediate points thereof, or in other words, in the vicinity of the connection between the buccal surface and the distal surface, the vicinity of the connection between the distal surface and the lingual surface, the vicinity of the connection between the lingual surface and the mesial surface, and the vicinity of the connection between the mesial surface and the buccal surface.

The supplementary form data generated in such a manner is added to the structure data 22 within the recording unit 11. In other words, the structure data 22 used thus far is overwritten by the supplementary form data generation unit.

The supplementary form data exhibits a significant effect in terms of attaching the frame to the anchor tooth at the proper orientation and the proper position. In addition, the supplementary form data can also ensure an appropriate cement space as per the settings.

Figure 22:
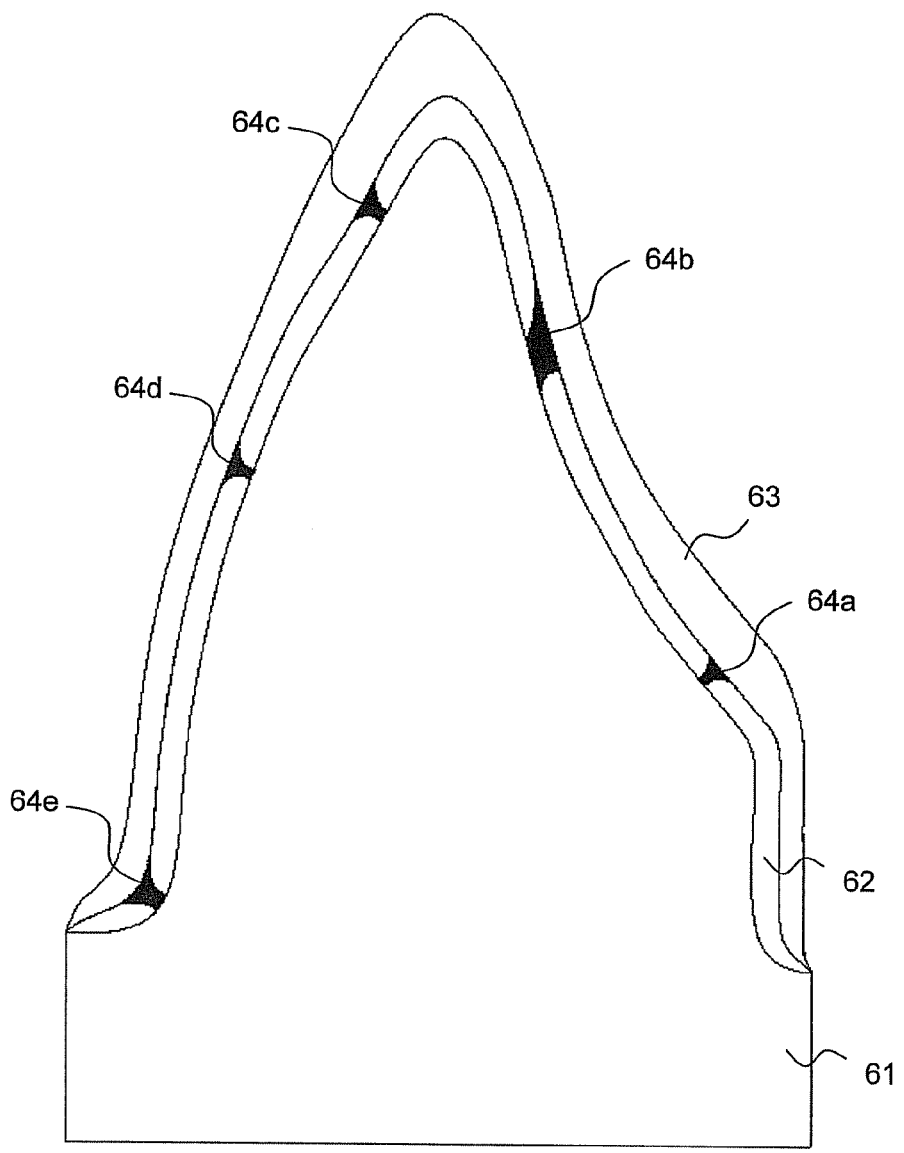
FIG. 22 illustrates the state of a cross-sectional view in which a crown manufactured according to the present invention has been attached to an anchor tooth, viewed from the side.

FIG. 22 is a cross-sectional view of a frame manufactured by the layered modeling apparatus 100 using the structure data 22 to which the supplementary form data has been added and attached to an anchor tooth, viewing the frame from the side. In the example shown in FIG. 22, the space between an anchor tooth 61 and a frame 63 has been filled with an adhesive material 62. Meanwhile, supplementary members 64a to 64e, which fix the position and orientation of the frame 63 relative to the anchor tooth 61, are provided between the anchor tooth 61 and the frame 63.

The supplementary form data created in light of the above-mentioned items has a significant effect in terms of ensuring an appropriate cement space with high precision. Furthermore, the supplementary form functions as a guide for uniquely determining the accurate orientation and position as per the design, preventing the occurrence of problems such as play in the cement space becoming an obstruction to accurate positioning when attaching a model such as a frame to an anchor tooth.

These effects greatly reduce discrepancies when attaching the prosthesis to the patient and adjustment operations, and the amount of experience required for such operations is also reduced. This in turn contributes greatly to a reduction in the work performed by the technician and the burden and pain experienced by the patient.

The supplementary form data generation unit 27 can generate the supplementary form data in this manner, in cases where the structure to be modeled is a frame such as a crown or a bridge and it is necessary to add a cement space for luting or adhering the frame to an anchor tooth, position the frame relative to the anchor tooth so that the frame maintains the proper position and orientation, and so on.

(Step S4 Structure Data Correction Process)

In the structure data correction process of step S4, the correction unit 28 corrects the structure data 22 generated by the creation unit 15 or the supplementary form data generation unit 27 and recorded in the recording unit 11 based on the composition data 23, generates corrected structure data 29, and records the resultant in the recording unit 11.

Frames for crowns and bridges used in normal dentistry are often made of metal, ceramics, or the like. In addition, resins and ceramics are often used as materials that are built up on the top layer of the frame. In addition, metals, resins, and ceramics are used in prostheses that are fitted, using dental cement or bonding material, into cavities created through appropriate treatments, such as inlays and onlays.

A process for realizing the final strength of ceramic materials, through sintering (firing), is necessary. This makes it possible to provide a prosthesis that maintains its strength over a long period of time even in an environment in which stress is repeatedly applied at high humidities, that is chemically stable and has no adverse effects on organisms, and which accurately reproduces the brightness, transparence, and color tones of natural teeth.

In particular, materials that use alumina, zirconia, and so on as their primary components not only have the strength and durability to be employed in applications, such as crowns or bridges, hitherto limited to metals, but also have colors more in harmony with body tissues than metals. Such materials have therefore been garnering attention recently.

While the firing process does bring about the abovementioned advantages, it also has a problem in that it causes a change in dimensions, form, and so on, such as shrinkage, following the firing.

The structure data correction process of step S4 is used, for example, to eliminate problems such as shrinkage, a change in form, and a drop in precision due to the firing.

The correction unit 28 corrects shrinkage, distortion, and so on in the structure data 22 in advance, so that the post-firing structure is as close to the structure data 22 as possible. Hereinafter, an example is given in which the amount of shrinkage due to firing is corrected, but the corrections performed by the correction unit 28 are not limited to the shrinkage amount. For example, it is also possible to correct the amount of change caused by distortion and expansion in the firing process. The composition data 23 and change amount data 30 are used in the calculation of this correction amount (shrinkage amount). The composition data 23 is data expressing the composition of the materials used in the structure that is to be modeled through layering performed by the layered modeling apparatus 100. For example, in the case where the stated frame is to be modeled through layered modeling of powdered zirconia, data indicating the powdered zirconia and the relative density thereof is recorded in the composition data 23.

The change amount data 20 is data in which the compositions of various materials that can be used in the structure to be modeled through layering and change amount data indicating the amount of change caused by sintering for each of those materials are recorded in association with one another. The following Table 1 indicates an example of the content of the change amount data 20. In the example shown in Table 1 below, the composition, relative density, and amount of shrinkage due to the sintering of the model are recorded as a combination record. Note that the content of the change amount data 20 is not limited to that in Table 1 below.

TABLE 1

| Model Composition | Relative Density | Shrinkage Amount |
|---|---|---|
| Zirconia | 5.82 | 19.5 |
| Zirconia | 6.7 | 22.5 |
| Alumina | 3.74 | 0.8 |
| Alumina | 3.98 | 1.0 |
| ... | ... | ... |

When, for example, modeling powdered zirconia through layered modeling, if the relative density of the model indicated in the composition data 23 is 5.82, the correction unit 28 refers to the change amount data 20 indicated in the above Table 1, and can thereby obtain a shrinkage amount for zirconia of 19.5 for the relative density of 5.82. The correction unit 28 enlarges the structure indicated by the structure data 22 by an amount corresponding to the shrinkage amount of 19.5, thereby generating the corrected structure data 29.

Through this, the corrected structure data 29, which anticipates the shrinkage that occurs due to firing, is obtained. The corrected structure data 29 is recorded in the recording unit 11.

Note that a calculation formula for enlargement/reduction used in, for example, three-dimensional CAD or CAM, can be applied to the calculation of the enlargement/reduction of the structure. For example, the enlargement/reduction can be performed by relocating the various parts of the structure at distances obtained by scaling the distances from a source point to each of the parts of the structure as necessary. In addition, the correction unit 28 may correct the structure data 22 having applied a coordinate conversion formula in three-dimensional space (for example, an affine transformation or the like).

Although the correction unit 28 performs the correction in the above example using the shrinkage amount included in the change amount data 30, it should be noted that the configuration may be such that the correction unit 28 calculates the shrinkage amount using the change amount data 30. For example, by recording functions for finding the shrinkage amount from the relative density for each material as the change amount data 30, the correction unit 28 can calculate the shrinkage amounts using those functions.

In addition, the correction unit 28 is not limited to correcting the shrinkage caused by sintering, as in the abovementioned example. For example, the correction unit 28 may calculate the amount of change due to the drying, polymerization, and so on of the material, such as resin, from the change amount data, and perform a correction for correcting that distortion. Note that the mechanisms and degrees of distortion, the trends in changes in the form, and so on differ between the case where a material such as resin distorts due to drying, polymerization, and so on, and the case where ceramics distort due to sintering. In the case where both types of distortion are to be corrected, change amount data, calculation of the change amount, and correction calculations are necessary for each type of distortion. In this manner, the correction unit 28 can make appropriate corrections in accordance with various materials, distortion mechanisms, and so on.

In addition, two phenomena, or a change in dimensions and change in form caused thereby, often occur in both cases of change caused by drying, polymerization, and so on and in cases of change caused by sintering. For this reason, the correction unit 28 may perform change amount calculations and correction calculations for each of these phenomena.

(Step S5 Support Member Data Generation Process)

In the support member data generation process of step S5, the contour generation unit 5 and the support member generation unit 7 use the corrected structure data 29 created by the correction unit 28 to create support member data 25 expressing the form of a support member that supports the structure. Hereinafter, a case where the structure expressed by the corrected structure data 29 is a bridge frame as described in step S4 shall be given as an example.

Figure 3B:
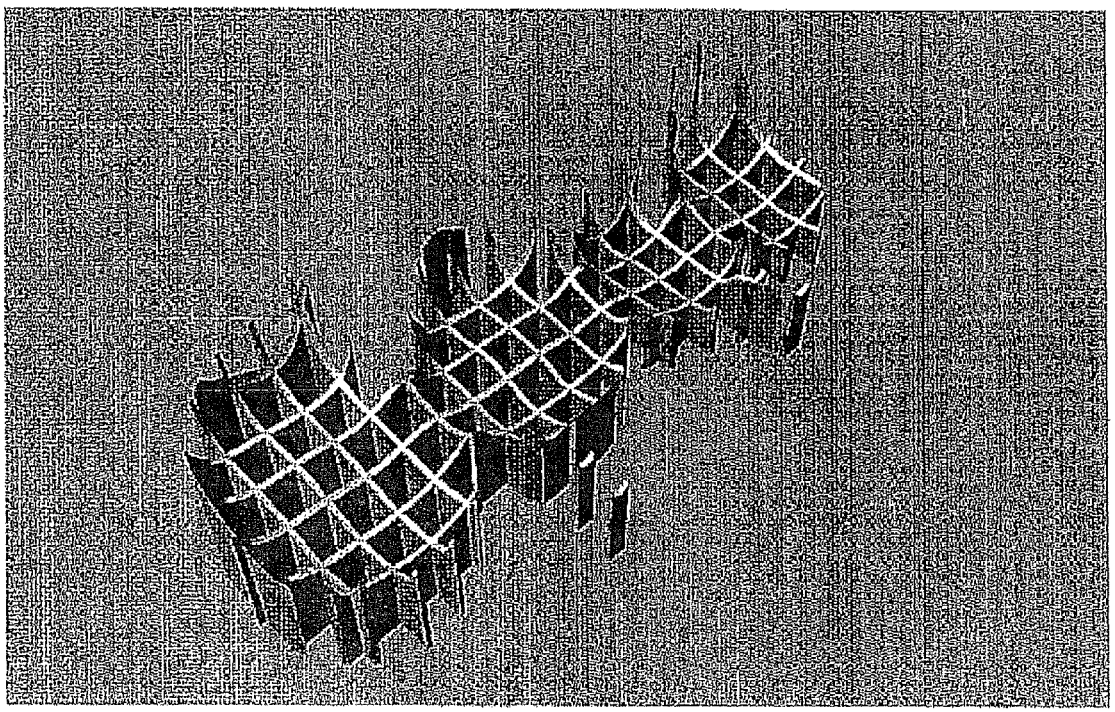
FIG. 3B is a diagram illustrating an example of a support member expressed by support member data 25 created by a support member generation unit 7.

FIG. 3B is a diagram illustrating an example of the support member expressed by support member data 25 created by the support member generation unit 7. The support member shown in FIG. 3B is a support member for supporting the frame shown in FIG. 3A upon a modeling table, described later, when that frame is formed by the layered modeling apparatus 100. In other words, a frame, which is the structure shown in FIG. 3A, is formed upon the support member shown in FIG. 3B.

Figure 4:
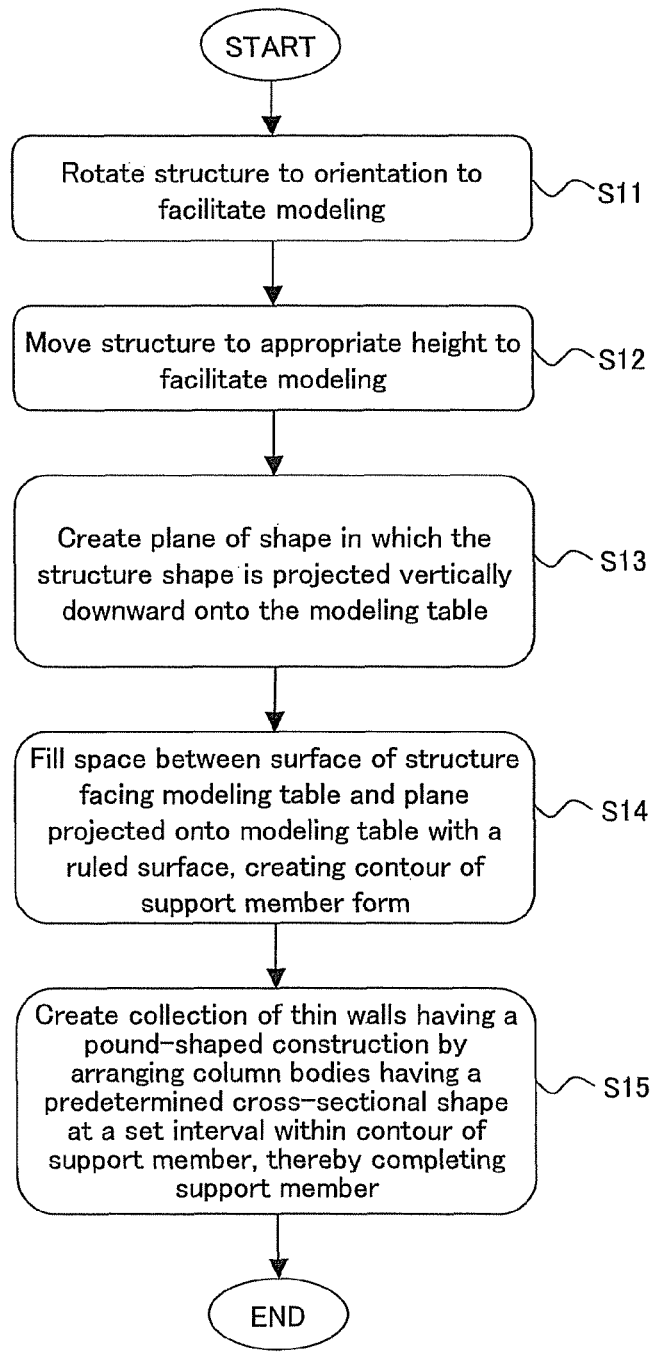
FIG. 4 is a flowchart illustrating an example of the process for creating the support member data 25.

FIG. 4 is a flowchart illustrating an example of the process for creating the support member data 25. First, the contour generation unit 5 loads the corrected structure data 29 recorded in the recording unit 11, and rotates the structure expressed by the corrected structure data 29 relative to the base plane to an orientation that enables easy modeling (step S11). The base plane is a plane that forms the base of the modeling layers that are layered in order to form the structure. In the processing performed by the modeling data creating system 1, the base plane can be taken as, for example, an xy plane. Note that in the layered modeling apparatus 100, the base plane is, for example, a modeling table.

The form of the space between the base plane and the structure changes depending on the orientation at which the frame, which is the structure expressed by the corrected structure data 29, is arranged relative to the base plane. If the form of the space between the base plane and the structure changes, the form of the support member that is disposed in that space also changes. Accordingly, it is preferable to determine the arrangement of the structure so that the amount of material used for the support member is at a minimum, or so that the modeling time for the support member and the structure is at a minimum. It is preferable to determine the arrangement of the structure relative to the base plane so as to prioritize one of these factors for determining the arrangement or to balance them both.

Meanwhile, in this step, when the frame is arranged with its anchor tooth-side surface facing downward (toward the base plane), the side of the frame facing the anchor tooth is supported by the support member. With such a configuration, there are cases where the border between the supplementary member and the support member is unclear. In addition, because the amount of space on the side that makes contact with the anchor tooth is small, it is often difficult to fit fingers or tools into that space during the process for removing the supplementary member after the modeling and firing processes have ended, and thus difficult to remove the supplementary form. It is thus preferable for the support member data to be generated so that the surface of the frame on the anchor tooth side is facing upward, so as to preempt the occurrence of this problem and enable the removal process to be executed smoothly.

The contour generation unit 5 calculates the volume of the space between the base plane and the structure for a variety of arrangements by, for example, rotating the structure. The contour generation unit 5 can select, from among the variety of arrangements, an arrangement in which, for example, the stated volume is minimum as the arrangement to be used when forming the structure.

Figure 5:
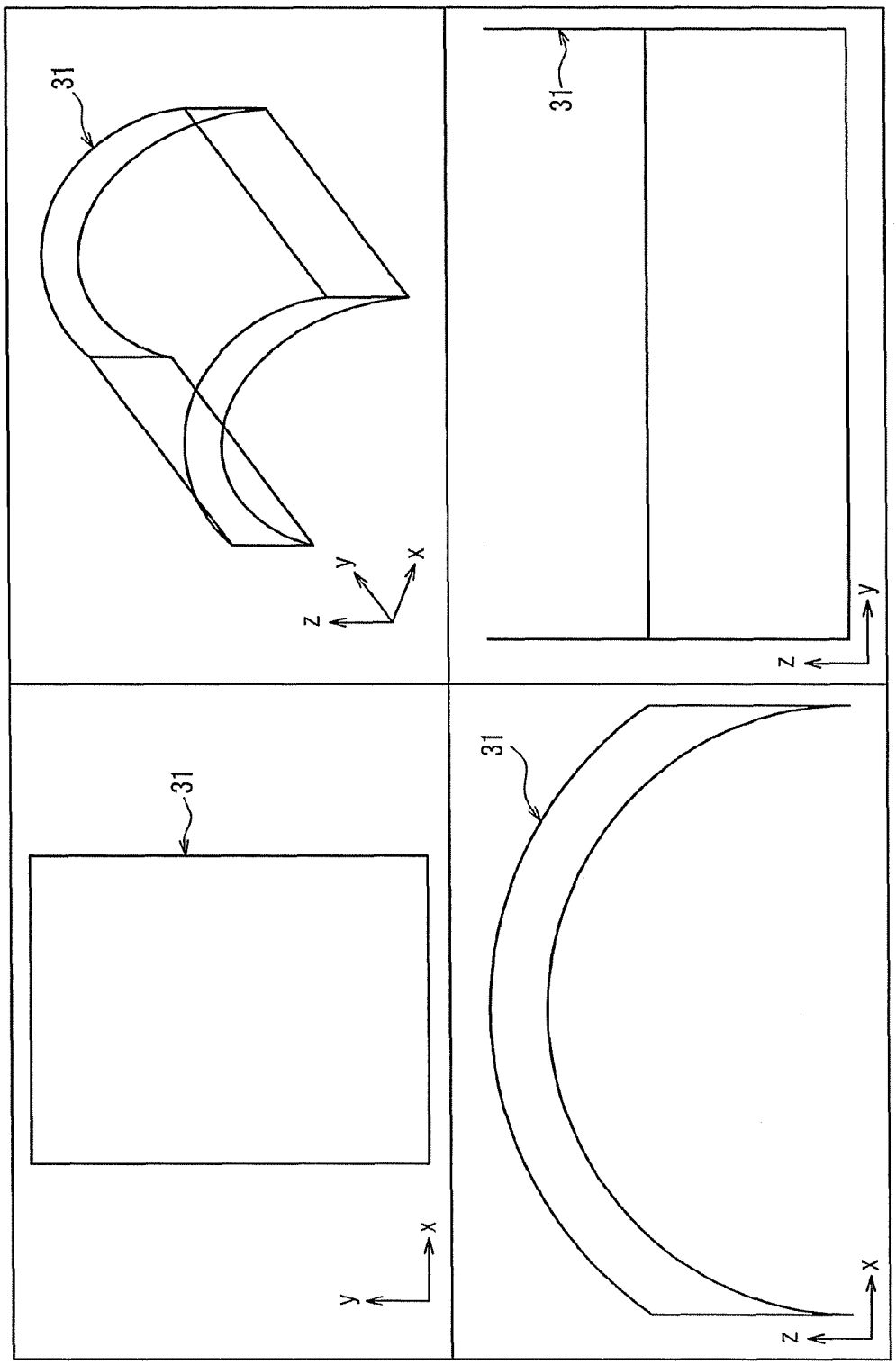
FIG. 5 is a diagram illustrating an example of a screen that displays the state in which a structure 31 expressed by structure data 22 is arranged upon xyz coordinates.

FIG. 5 is a diagram illustrating an example of a screen that displays the state in which a structure 31 expressed by the corrected structure data 29 is arranged upon xyz coordinates. In the screen shown in FIG. 5, the top-right image expresses the form of the structure 31 as viewed at an angle from above; the bottom-right image expresses the form of the structure 31 as viewed from the x-axis direction; the top-left image expresses the form of the structure 31 as viewed from the z-axis direction; and the bottom-left image expresses the form of the structure 31 as viewed from the y-axis direction. The xyz coordinates in the screen shown in FIG. 5 can be assumed to be coordinates in which, for example, the direction perpendicular to the base plane is taken as the z-axis, and the surface of the base plane corresponds to an xy plane. Note that the form of the structure 31 shown in the screen in FIG. 5 is not the form of the frame, but is rather a simplified form, in order to simplify the descriptions. Like FIG. 5, the subsequent FIGS. 6 to 13 also depict the structure 31 expressed by the corrected structure data 29 and the support member expressed by the support member data 25 as a simplified form.

The contour generation unit 5 determines the height of the structure 31 expressed by the corrected structure data 29 relative to the base plane to be a height suited for modeling ease (step S12). The contour generation unit 5 can set data expressing a height that is pre-set in the recording unit 11 as the height of the structure 31 relative to the base plane. In order to reduce the amount of material used in the support member, it is preferable for the height of the structure 31 relative to the base plane to be as low as possible. However, if the structure is too low relative to the base plane, it is difficult to remove the structure from the support member, and thus it is preferable for the height to be of a degree that enables the easy removal of the structure.

Figure 6:
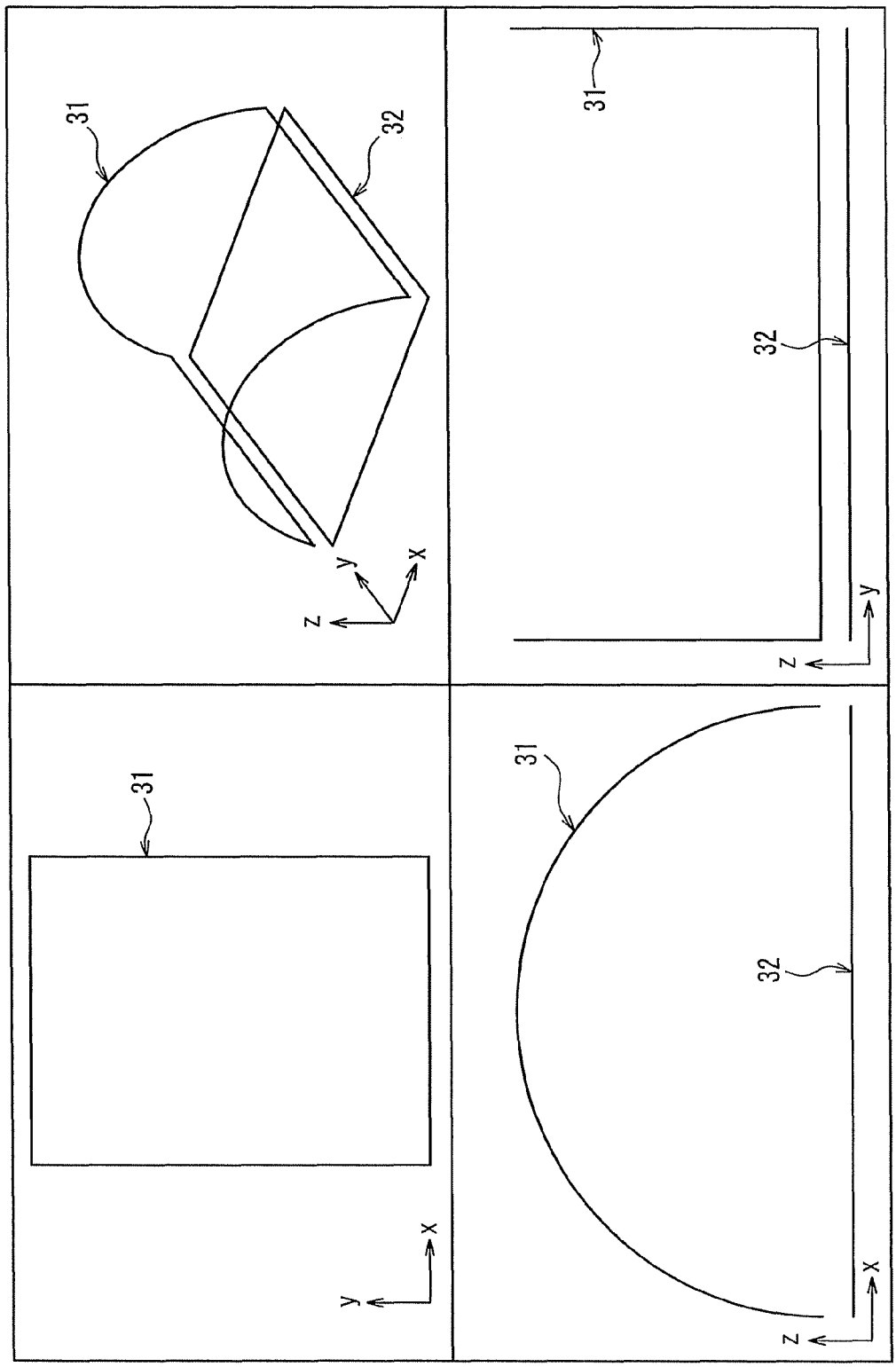
FIG. 6 is a diagram illustrating an example of a screen that displays a plane 32 in which the form of the structure 31 is projected onto the xy plane.

The contour generation unit 5 creates a plane of a shape obtained by projecting the form of the structure 31 from the z-axis direction onto the xy plane, or in other words, onto the base plane (step S13). FIG. 6 is a diagram illustrating an example of a screen that displays a plane 32 in which the form of the structure 31 is projected onto the xy plane.

Figure 7:
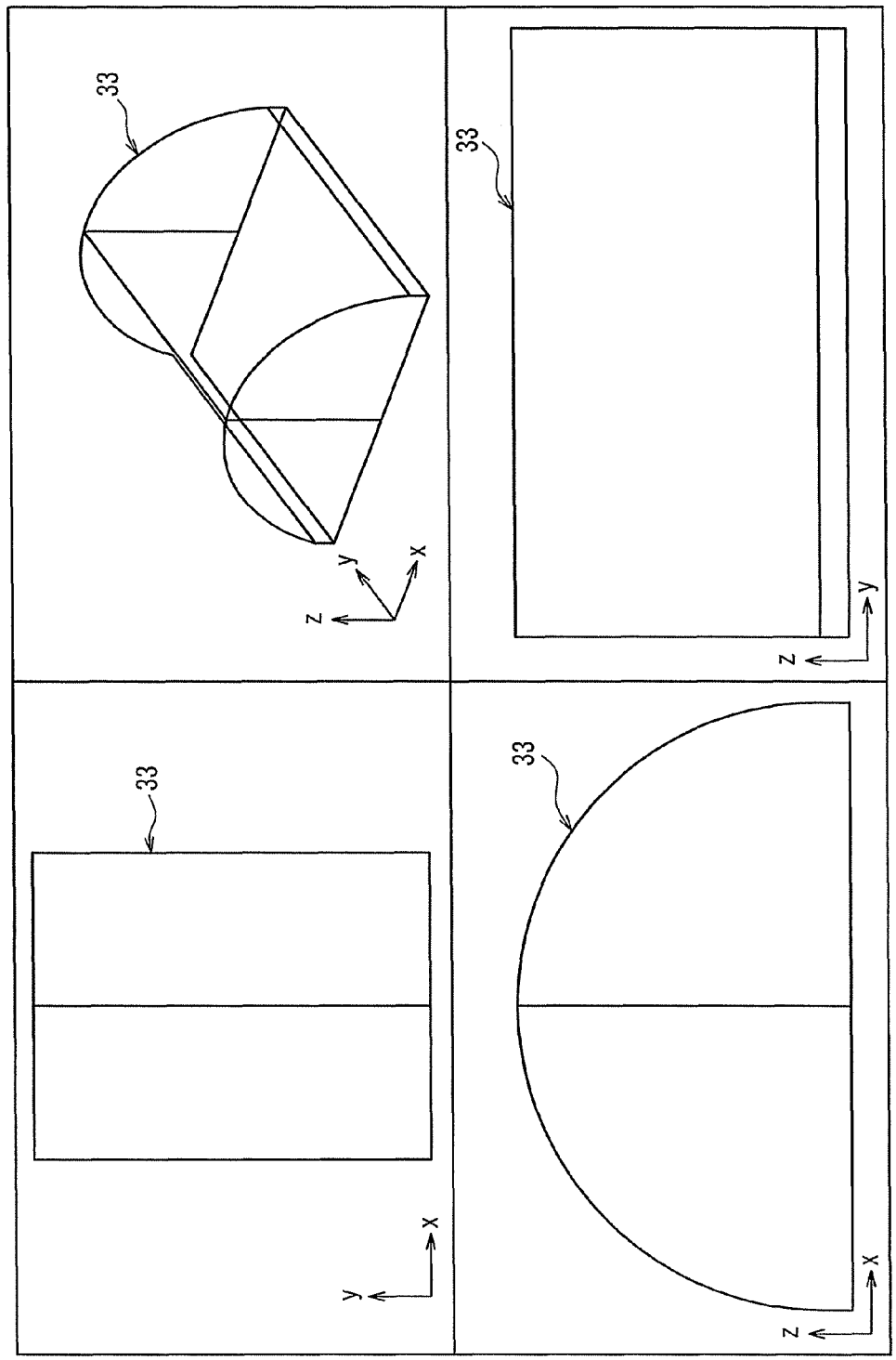
FIG. 7 is a diagram illustrating an example of a screen that displays a contour 33 expressed by contour data.

The contour generation unit 5 generates a contour of the space between the plane 32, obtained by projecting the structure 31, and the structure 31 itself by, for example, filling that space with a ruled surface. FIG. 7 is a diagram illustrating an example of a screen that displays a contour 33 of the space between the structure 31 and the base plane (xy plane), as expressed by the contour data 24. For example, in the case where the structure 31 is a frame, data that expresses the contour of the space between a surface created by the maximum contour line of the frame and the plane 32 obtained by projecting the frame onto the base plane is the contour data 24. The contour data 24 need not express a contour encompassing the entire periphery of the space; data that expresses at least a partial contour is sufficient.

The format of the contour data 24 may be, for example, a closed surface or solid. The format of the contour data 24 depends, for example, on the format of the data handled by the software that implements the functionality of the contour generation unit 5.

Figure 8:
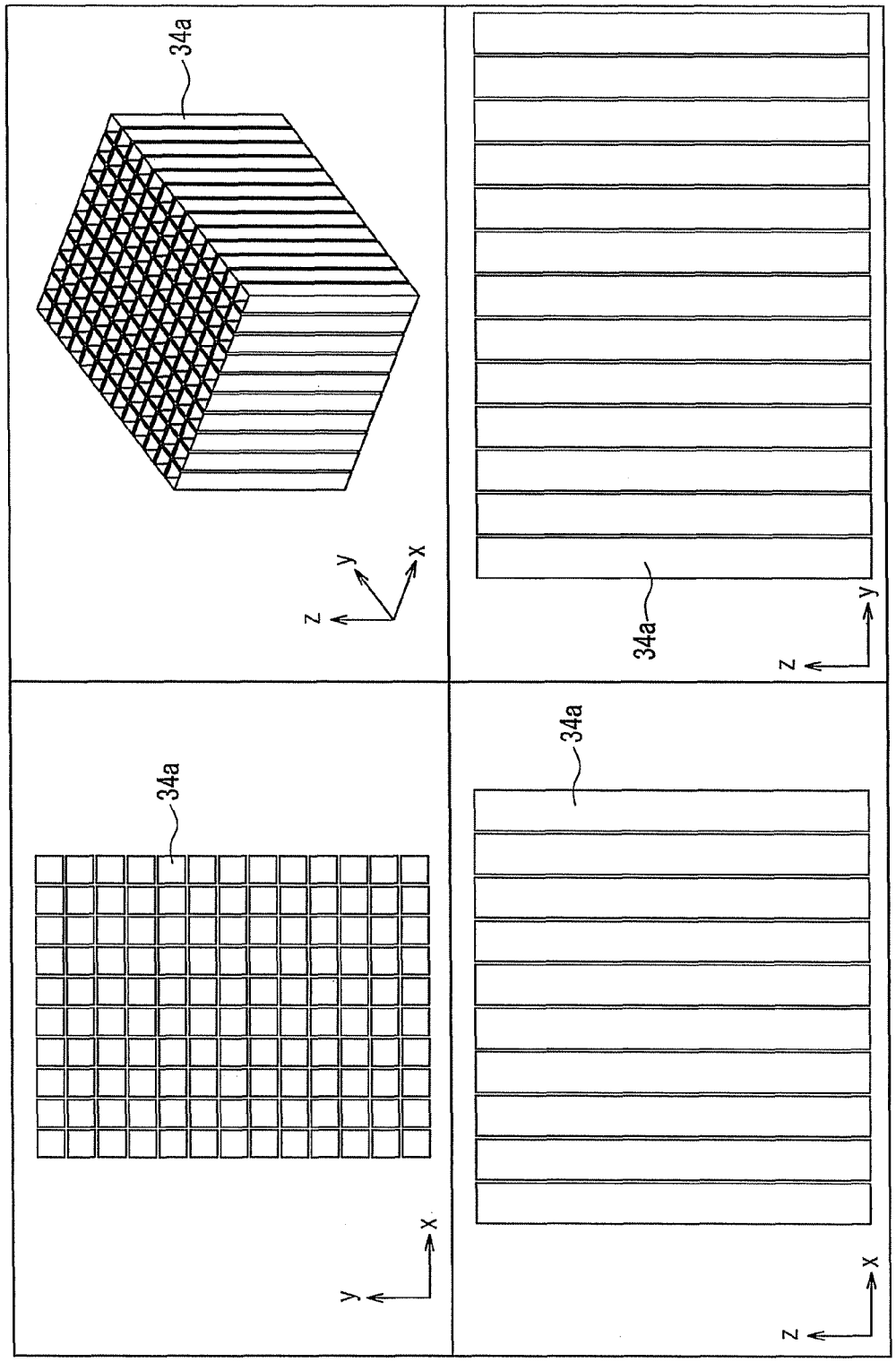
FIG. 8 is a diagram illustrating an example of a screen that displays column bodies 34a arranged at equal intervals perpendicular to the xy plane.

The support member generation unit 7 generates a support member 34 by arranging multiple column bodies or plate bodies having a predetermined cross-sectional form within the space expressed by the contour data 24. The support member 34 is formed, for example, of multiple column bodies or plate bodies arranged, at constant intervals, perpendicular to the xy plane. FIG. 8 is a diagram illustrating an example of a screen that displays column bodies 34a arranged at equal intervals perpendicular to the xy plane. As per the example shown in FIG. 8, a collection of thin walls having a pound-shaped construction can be used as the support member 34. The support member 34 may have a construction in which plate bodies perpendicular to the xy plane intersect with one another vertically and horizontally.

A method that uses logical operations or a method that simply arranges the column bodies or plate bodies and trims them using the contour expressed by the contour data 24 can be given as examples of the method by which the support member generation unit 7 generates the support member data 25 expressing the form of the support member 34.

Figure 9:
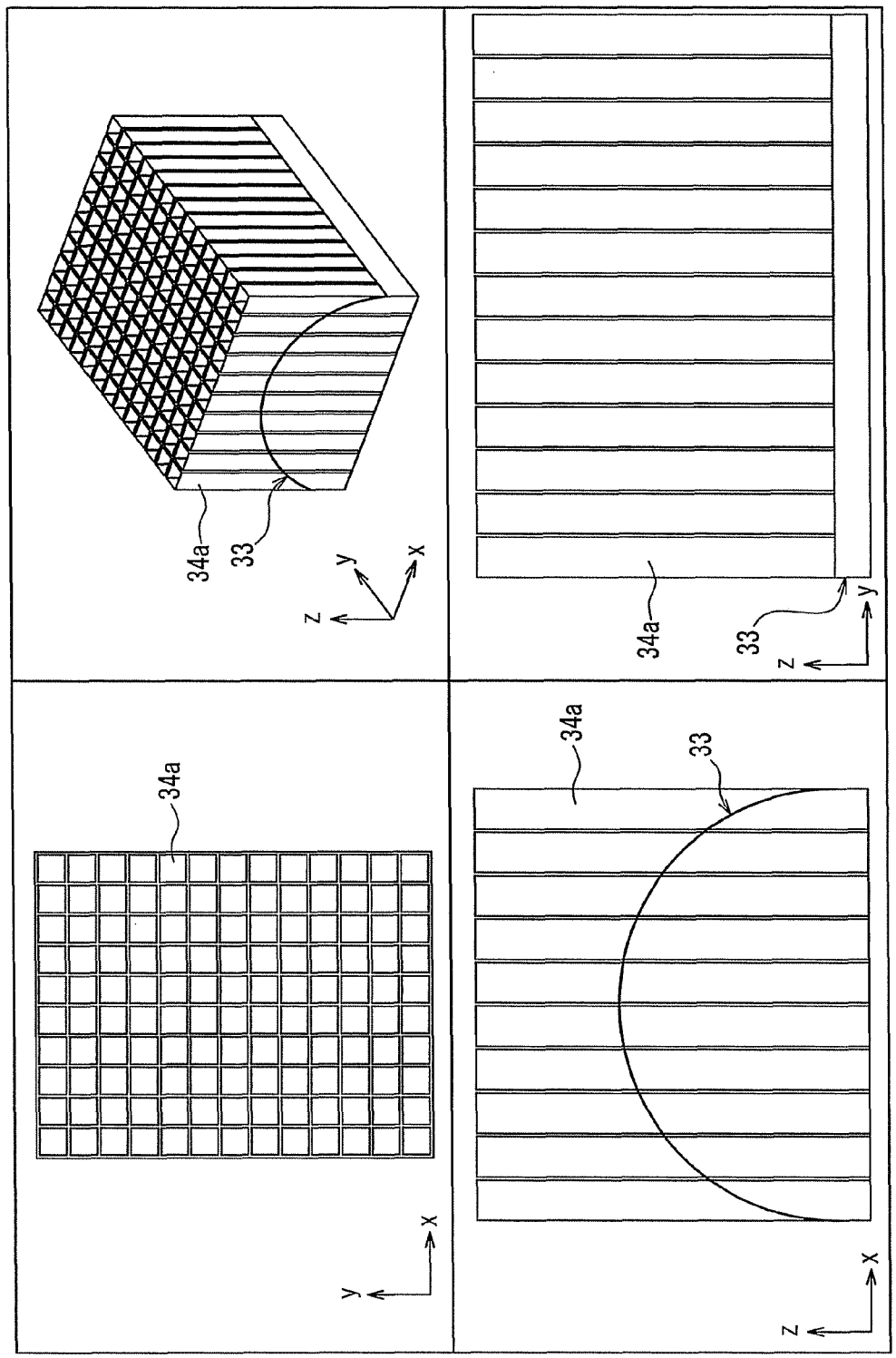
Figure 10:
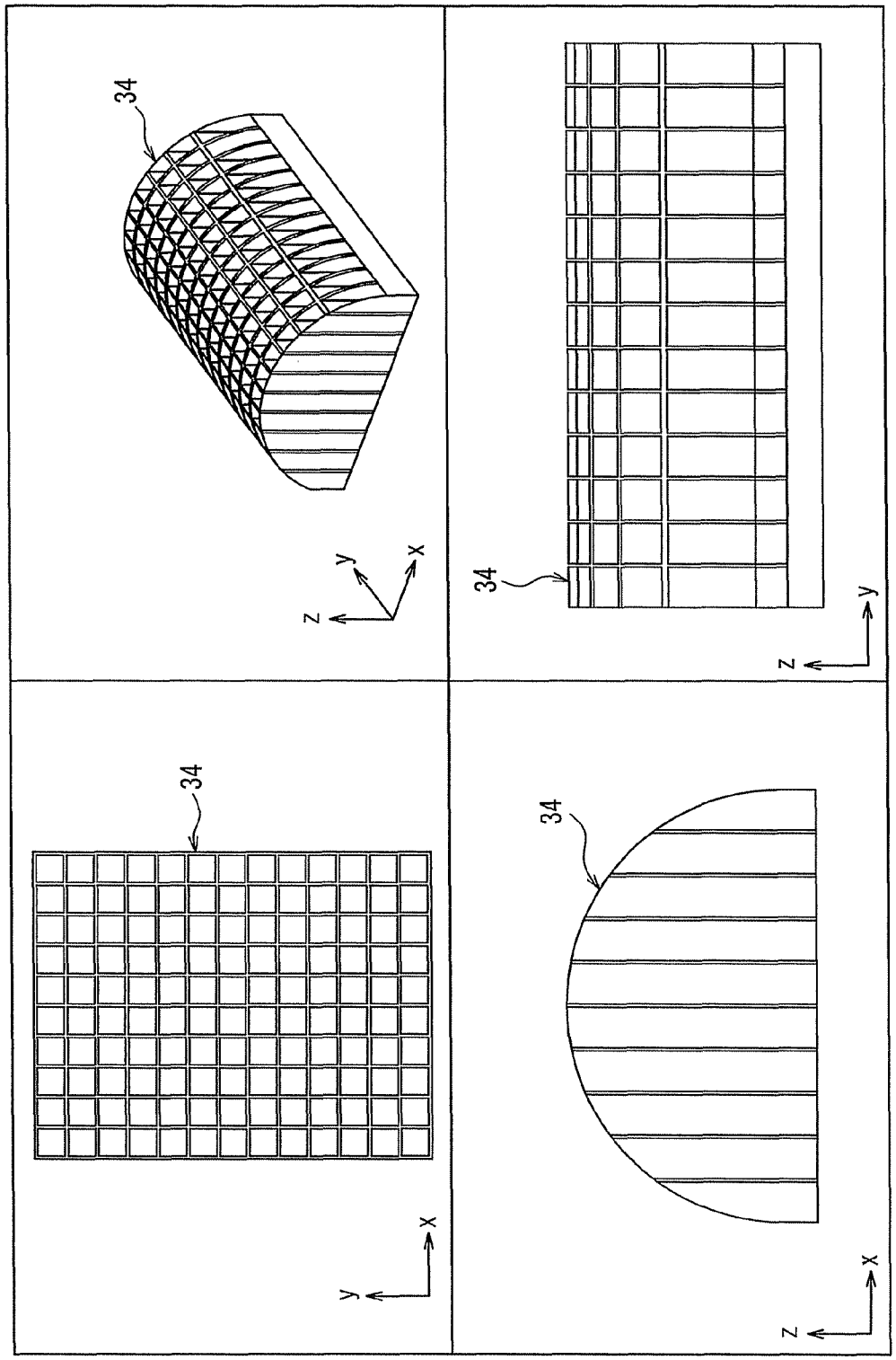
Figure 11:
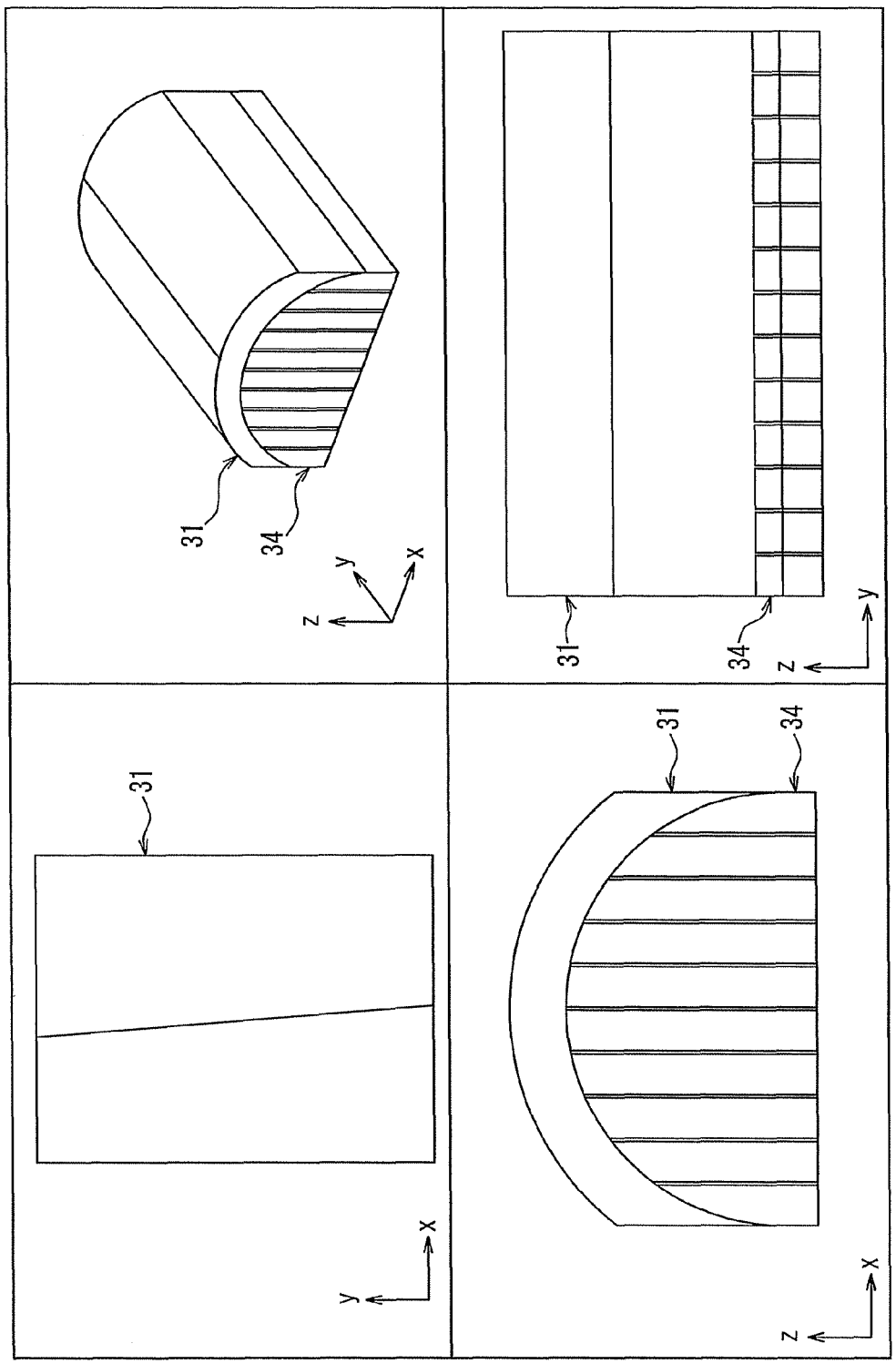
FIG. 11 is a diagram illustrating an example of a screen that displays a state in which the structure 31 is supported upon the support member 34.

An example of the method for generating the support member data 25 using logical operations shall be described. For example, the support member generation unit 7 performs an AND operation using data of the form that defines the contour 33 of the support member 34 (see FIG. 7) and the data of the column bodies 34a arranged at equal intervals as shown in FIG. 8 (see FIG. 8). FIG. 9 is a diagram illustrating an example of a screen that displays a state in which the contour 33 has been superimposed upon the column bodies 34a. As a result of the AND operation, only the portions that contain the forms of both the contour 33 and the column bodies 34a remain, and thus the form of the support member 34 is obtained. FIG. 10 is an example of a screen that displays the form of the support member 34. By performing an OR operation using the form of the support member 34 shown in FIG. 10 and the form of the target structure 31 (see FIG. 5), the two forms are added together. As a result, the form of the model to be modeled is obtained. The form of the model obtained in such a manner is a form in which the form of the target structure 31 and the form of the support member 34 have been combined with each other. FIG. 11 is a diagram illustrating an example of a screen that displays a model configured from the target structure 31 and the support member 34. The screen in FIG. 11 indicates a state in which the structure 31 is supported upon the support member 34.

Next, an example of generating the support member data 25 through trimming shall be described. Support member data 25 expressing the form of the support member 34 is generated by superimposing the contour 33 (see FIG. 7) upon the column bodies 34a arranged as shown in FIG. 8 and trimming the column bodies 34a. FIG. 9 is a diagram illustrating an example of a screen that displays a state in which the contour 33 has been superimposed upon the column bodies 34a. The support member generation unit 7 creates the form of the support member 34 by trimming the portions of the column bodies 34a that fall outside of the portions contained within the contour 33. The form of the support member 34 formed by trimmed column bodies 34a is displayed, for example, as shown in FIG. 10.

The form of the support member 34 created in this manner is required to be a form that can support the structure 31 upon the base plane. FIG. 11 is a diagram illustrating an example of a screen that displays a state in which the structure 31 is supported upon the support member 34. As shown in FIG. 11, the support member 34 has a construction that supports the entire surface of the structure 31 on the base plane (xy plane) side. With such a construction, the structure 31 is prevented from changing form during the firing process; for example, collapsing, sagging during vitrification, distorting, and so on.

It is preferable for the cross-sectional form of the column bodies to be square or rectangular. In such a case, the side surfaces of the columns are walls. The strength of the support member 34 changes depending on the thickness of these walls and the length of one side of the square or rectangle in the cross-sectional form of the column bodies. In addition, the strength of the support member 34 also depends on the strength of the material used for the support member 34. It is desirable for the strength of the support member 34 to be of a degree whereby the support member 34 is not crushed under the weight of the structure 31 during modeling, and not crushed under the weight of the structure 31 during sintering. On the other hand, if the thickness of the walls is too great, the surface area of the support member 34 that makes contact with the structure 31 increases, making it more likely for remnants of the support member 34 to remain on the structure 31 after the support member 34 has been removed from the structure 31 following sintering.

Therefore, it is preferable for the walls between the column bodies of which the support member 34 is configured to be thick enough so the structure 31 does not distort during modeling, and thin enough so that the support member 34 can be easily removed by hand after modeling has ended or after sintering and so that remnants of the support member 34 do not remain on the structure 31 after the support member 34 has been removed. The support member generation unit 7 can set the thickness of the walls if the composition of the material used for the support member 34 has been determined. Hereinafter, an example of a method for finding the thickness of the walls of the column bodies of which the support member 34 is configured shall be described.

(Example of Method for Calculating Wall Thickness of Support Member 34)

It is preferable for the composition data 23, expressing the composition of the material used for the support member 34, to be recorded in the recording unit 11 in advance. For example, the designer of the structure 31 may set the composition of the material used as the support member 34 in the composition data 23. The support member generation unit 7 can calculate the thickness of the walls of the support member 34 based on the composition data 23 that has been set.

The stated measurement data is obtained by, for example, using the layered modeling apparatus to create a test piece having a constant form by distributing powder at a thickness of a single layer and ejecting a solution thereon, shaping the piece. The amount of shrinkage and distortion in the test piece following the firing is then measured and compared with the pre-firing dimensions.

It is preferable for the stated data expressing the form and material of the structure 31, the stated measurement data, and so on to be recorded in the recording unit 11 in advance. The support member generation unit 7 can use this data to find the parts and the directions and sizes thereof that experience shrinkage, sagging, and so on, using a general computation method, such as the finite-element method. The calculated data that expresses the parts and the directions and sizes thereof that experience distortion is used to find the thickness of the walls of the support member 34.

In addition, the support member generation unit 7 may use the weight distribution of the structure 31 (for example, the weight per unit of surface area when the structure 31 is projected onto a plane) to calculate the thickness of the walls of the support member 34. In the case where the weight applied to the support member 34 differs depending on the location, there is also the possibility that the thickness of the walls of the support member 34 changes depending on the location. For example, the support member generation unit 7 can increase the thickness of the walls of the support member 34 in areas where the weight per unit of surface area is greater.

The support member itself manufactured in this manner experiences shrinkage due to sintering, and generally, the thickness thereof is reduced. This has an indirect effect of making it easy to remove the support member. In other words, because the support member data 25 is generated from the corrected structure data 29 and the contour data 24, the support member modeled based on the support member data 25 shrinks in the same manner as the structure (the frame) due to sintering. Accordingly, the cross-sectional surface area of the plate bodies or column bodies of which the support member is configured is also reduced due to the shrinkage, reducing the strength. As a result, there is an advantage in that the support member can be more easily removed from the structure following the firing.

(Example of Form of Portion where Support Member 34 Makes Contact with Structure 31)

Here, an example of the form of the portion where the support member 34 makes contact with the structure 31 shall be described. After the model expressed by the support member data 25 and the corrected structure data 29 has been modeled by the layered modeling apparatus 100, or after the firing process has ended, the support member 34 is removed from the structure 31. Post-processing (retrieval, polishing, buffing,) is carried out on the structure after the support member 34 has been removed, thereby smoothing out the surface. Which portion the support member 34 is broken off at when the support member 34 is removed significantly influences the amount of work and time required for the post-processing. It is preferable for the vicinity of the portion where the structure 31 and the support member 34 make contact to break, in order to make the post-processing easy. In other words, it is preferable to generate the support member data 25 expressing a form in which when the support member 34 is removed from the structure 31, the remnants thereof do not remain on the structure 31.

It is preferable for the support member generation unit 7 to calculate the wall thickness of the support member 34 so that the surface area of the portion where the support member 34 and the structure 31 come into contact with each other is as small as possible. If the surface area of the portion where the support member 34 and the structure 31 come into contact with each other is small, the amount of remnants remaining on the structure 31 following the removal of the support member 34 is reduced.

In addition, the support member generation unit 7 can make the walls of the column bodies or plate bodies thinner at the portions where the column bodies or plate bodies of which the support member 34 is configured make contact with the structure 31 than at the other portions.

Figure 12A:
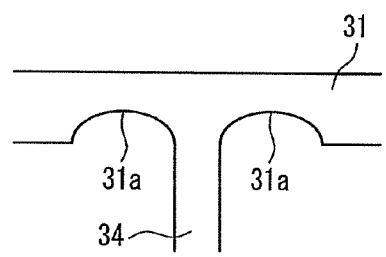
FIG. 12A is a diagram illustrating the cross-sectional shape of the support member 34 and the structure 31 in the case where the periphery of the portion that makes contact with the support member 34 is recessed.

In addition, the support member generation unit 7 may correct the structure data 22 so that the periphery of the portion of the structure 31 that makes contact with the support member 34 is recessed toward the inner surface of the structure 31. FIG. 12A is a diagram illustrating the cross-sectional shape of the support member 34 and the structure 31 in the case where the periphery of the portion that makes contact with the support member 34 is recessed. In the example shown in FIG. 12A, recesses 31a are provided in the periphery of the portion where the support member 34 and the structure 31 make contact with each other. It is preferable for the depth of the recesses 31a to be less than or equal to the thickness of the structure 31. This is to prevent the structure 31 from breaking.

It is also preferable for the size of the recesses 31a to be of a degree that can be eliminated through post-processing. For example, in the case where the structure 31 is a bridge frame, it is preferable for the surface area of the recesses 31a to be at a ratio of no more than 30% relative to the entire surface of the structure 31.

Figure 12B:
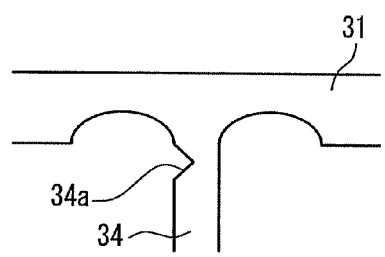
FIG. 12B is a diagram illustrating the cross-sectional shape of a support member 34 that has a notch.

In addition, the support member generation unit 7 may generate the support member data 25 expressing the support member 34 so that there is a notch in the vicinity of the portion that makes contact with the structure 31. FIG. 12B is a diagram illustrating the cross-sectional shape of a support member 34 that has a notch. In the example shown in FIG. 12B, a notch 34b is provided at the base of the portion where the support member 34 and the structure 31 make contact with each other. Through this, the support member 34 can be easily broken off at the notch 34a, which is close to the base, during removal, which reduces the chance of remnants remaining on the structure 31.

Note that the cross-sectional shape of the column bodies of which the support member 34 is configured is not limited to a square or rectangular shape. For example, the support member 34 may be configured of column bodies that have any cross-sectional shape, such a circle, an ellipse, a rhombus, a parallelogram, a pentagon, a hexagon, a lageniform, and so on. In other words, polygons having more than three sides, forms that have curved sides such as circles and wedges, and so on may be used as the cross-sectional shape. Two or more arbitrary types of such forms may be combined as well. Note that the cross-sectional shape of the supplementary member in step S3 can be configured as the same shape as the support member 34.

(Variation on Support Member 34)

Figure 13:
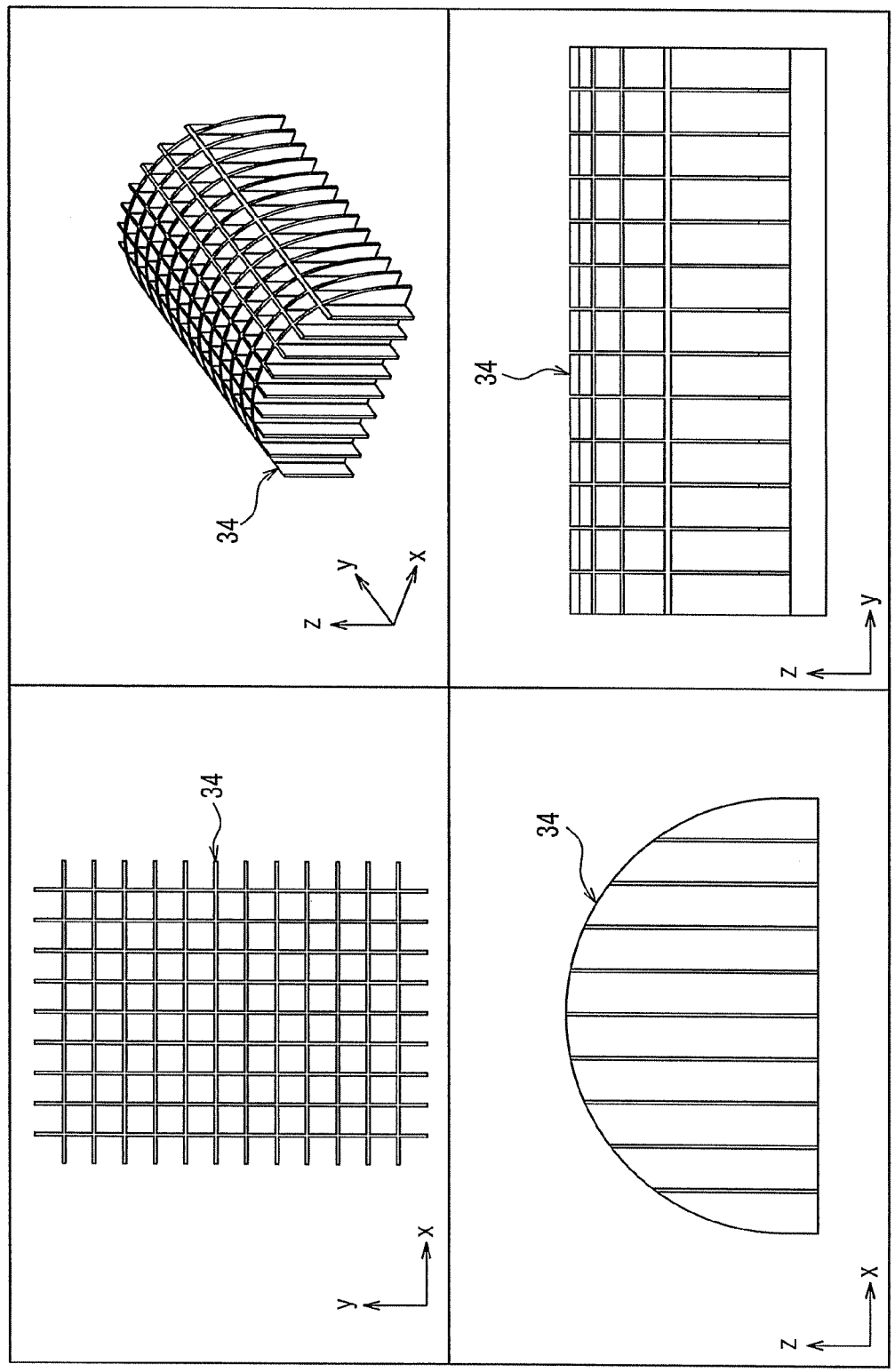
FIG. 13 is a diagram illustrating a screen that displays a variation on the support member 34.
Figure 14:
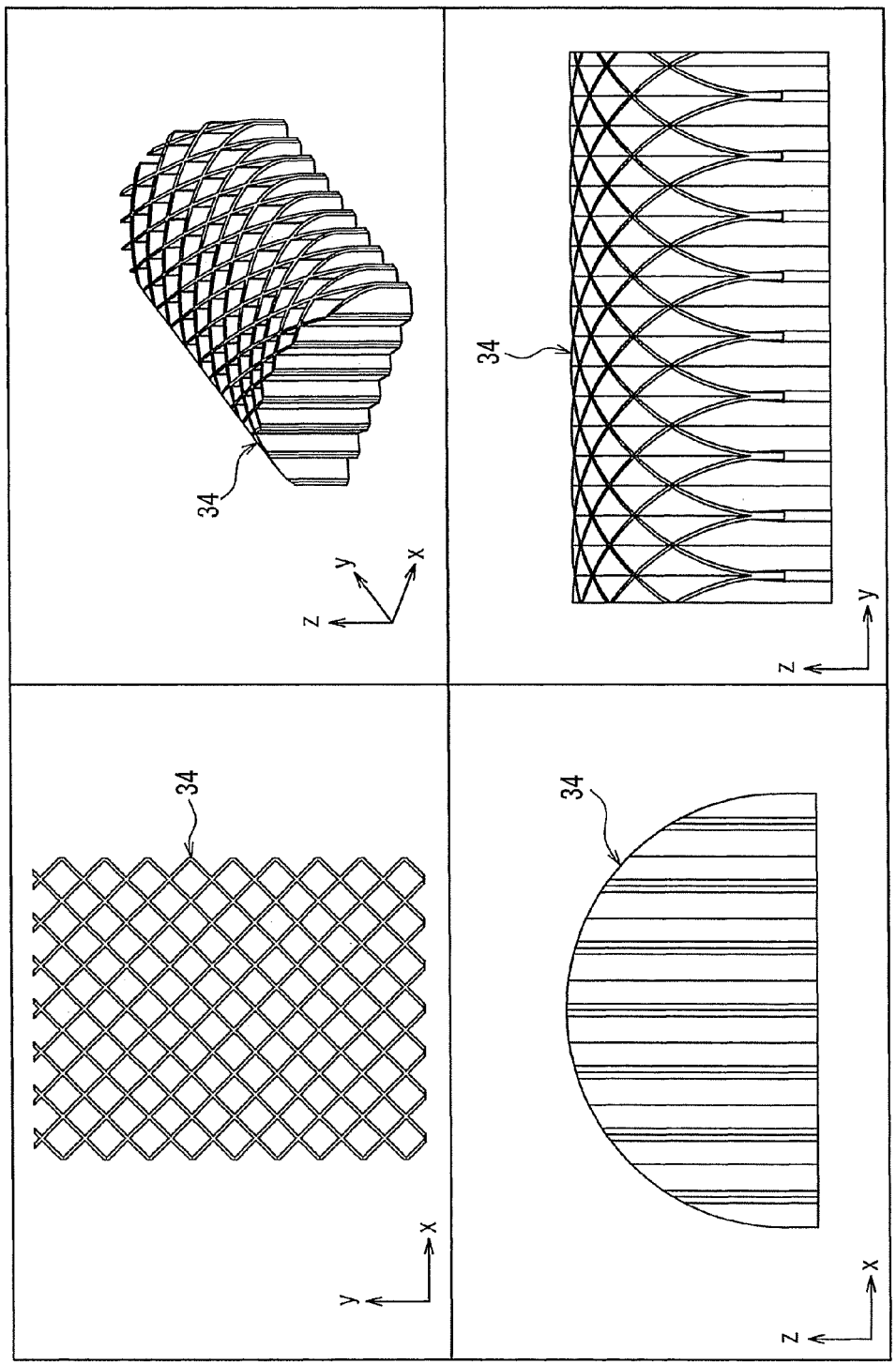
FIG. 14 is a diagram illustrating a screen that displays a variation on the support member 34.

FIGS. 13 and 14 are diagrams illustrating screens that display variations on the support member 34, which has a different form than the example of the support member 34 shown in FIG. 10. The form of the support member 34 shown in FIG. 13 is structured so that plate bodies perpendicular to the xy plane intersect vertically and horizontally, and the ends of the plate bodies project outward in the xy directions. With the support member 34 shown in FIG. 14, the cross-sectional shape of the column bodies of which the support member 34 is configured is a square that has sides at approximately 45° angles relative to the x-axis.

(Step S6 Cross-sectional Data Generation Process)

In step S6, the cross-section generation unit 9 generates the cross-sectional data 26 expressing the cross-sectional shapes of each of multiple planes, approximately parallel to the base plane, of the model configured of the support member 34 expressed by the support member data 25 and the structure 31 expressed by the corrected structure data 29.

Figure 15A:
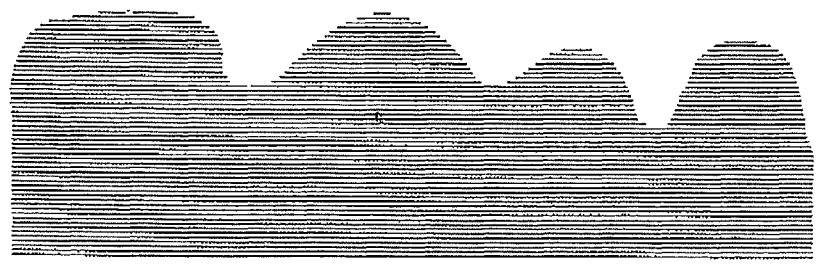
FIG. 15A is a diagram in which a bridge frame, which is the structure 31, is viewed from the side, in a state in which the bridge frame has been sliced along multiple parallel planes having predetermined intervals with respect to one another.
Figure 15B:
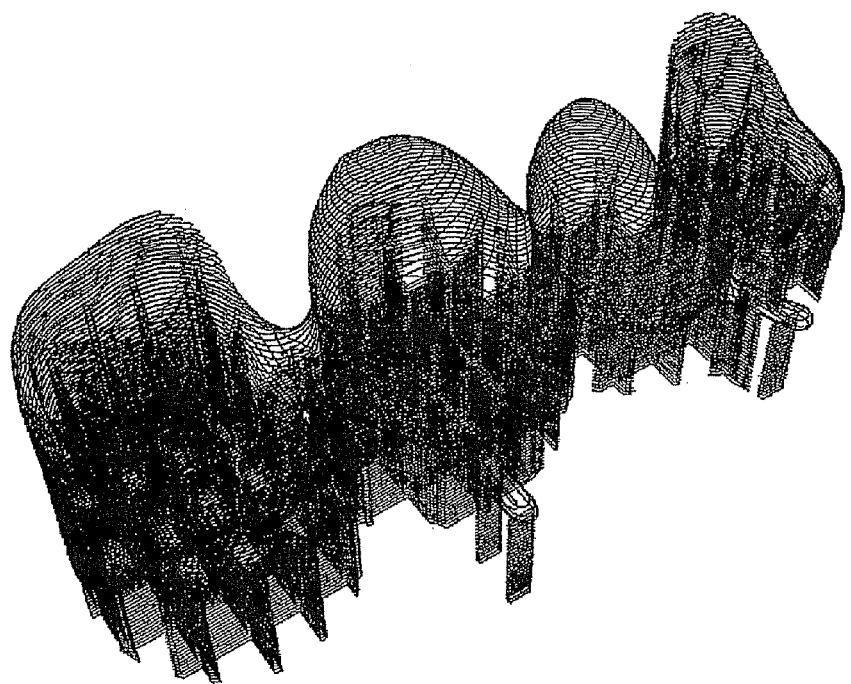
FIG. 15B is a diagram in which a bridge frame, which is the structure 31, is viewed at an angle from above, in a state in which the bridge frame has been sliced along multiple parallel planes having predetermined intervals with respect to one another.
Figure 15C:
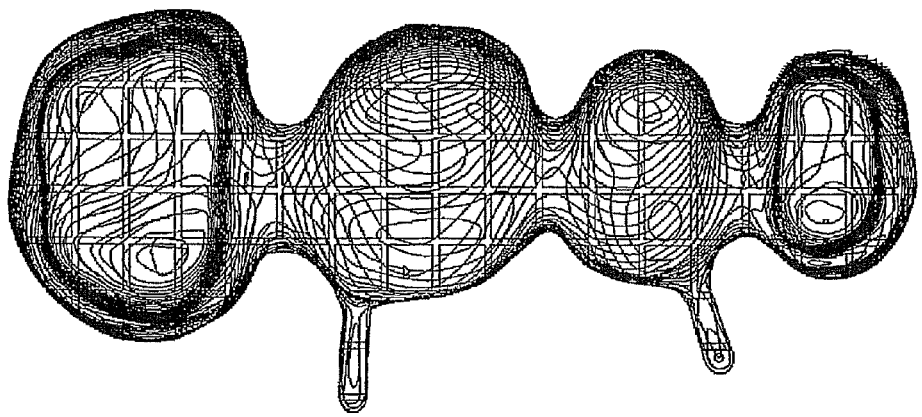
FIG. 15C is a diagram in which a bridge frame, which is the structure 31, is viewed from above, in a state in which the bridge frame has been sliced along multiple parallel planes having predetermined intervals with respect to one another.

FIGS. 15A to 15C are diagrams illustrating a state in which a model configured of the structure 31, which is a bridge frame, and the support member has been sliced along multiple parallel planes having predetermined intervals with respect to one another. In FIGS. 15A to 15C, the forms of the structure 31 or the support member in each cross-section obtained through the slicing are indicated by lines. FIG. 15A views the model from the side; FIG. 15B views the model at an angle from above; and FIG. 15C views the model from above.

As the cross-sectional data 26, the cross-section generation unit 9 generates, for example, a two-dimensional form of the structure 31 for each cross-section obtained by slicing the structure 31 at a predetermined interval (pitch), as shown in FIGS. 15A to 15C. It is preferable for the predetermined interval to be determined in accordance with the thickness of the modeling layer when modeling the structure 31.

Figure 16:
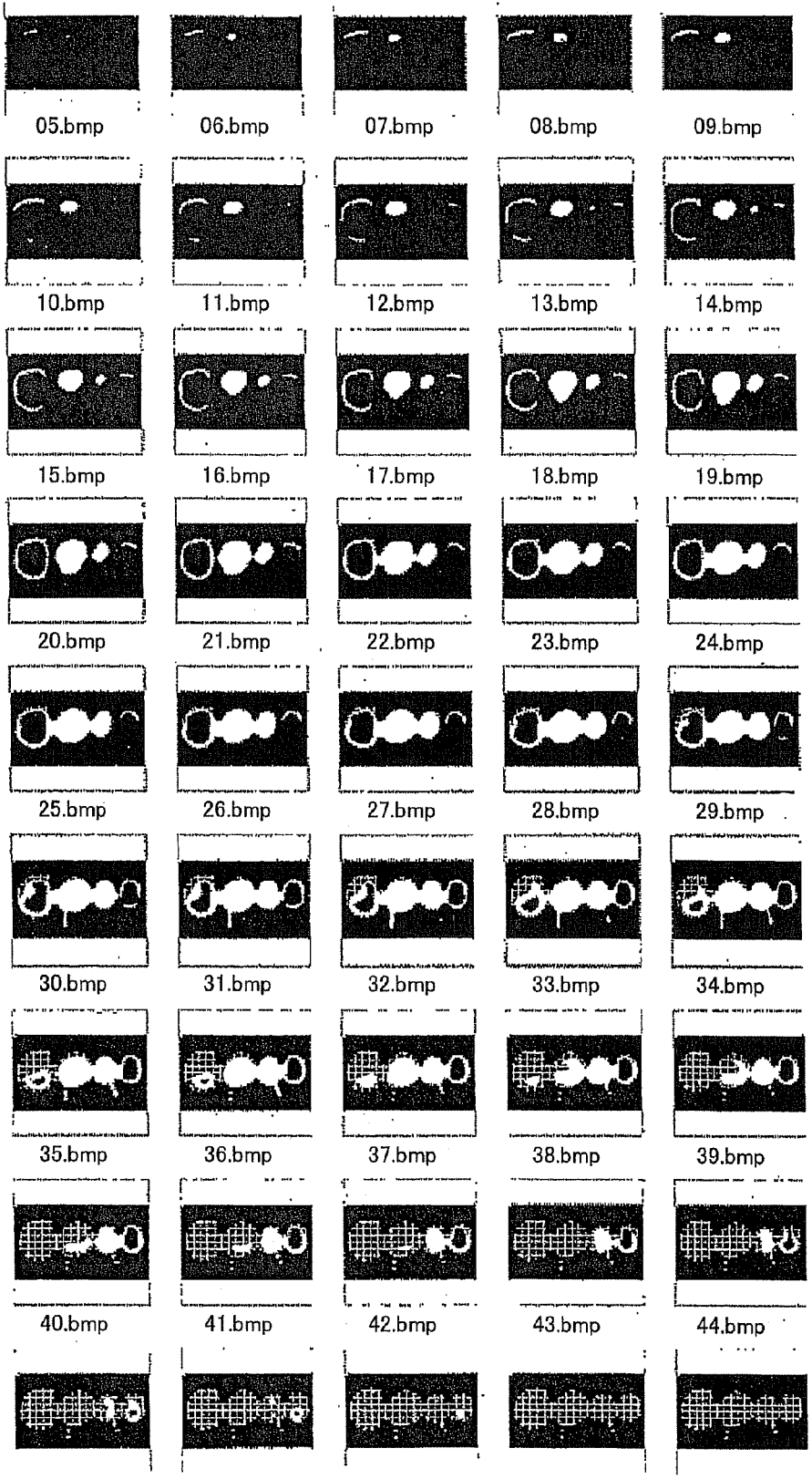
FIG. 16 is a diagram illustrating an example of image data for each cross-section of a bridge frame, which is the structure 31.

The cross-sectional data 26 is, for example, a group of image data expressing the two-dimensional forms of the cross-sections as bit maps. In each image of each cross-section, the portion corresponding to the structure 31 is expressed as gradation data indicating regions in which the structure 31 is to be formed. The form of the structure 31 in each cross-section may be indicated by changing the gradation depending on the material used to form the structure 31 or the color. FIG. 16 is a diagram illustrating an example of image data for each cross-section of the frame, which is the structure 31.

The cross-section generation unit 9 may correct the size of the image data so that the resolution of the image data expressing the two-dimensional forms of each cross-section is suited to the resolution of an ink jet head present in the layered modeling apparatus 100, which shall be discussed later. For example, in the case where the dot density of the ink jet head is 512 dots/36 mm (14.2 dots/mm), it is preferable to correct the size of the image data so that the bit spacing conforms thereto.

As discussed thus far, Embodiment 1 describes a case in which data for modeling a bridge frame, which is an example of a structure, is created. However, the structure is not limited to a bridge frame. For example, the structure may be a dental structure such as a corrective bracket or a corrective device, an inlay, an onlay, a crown, a bridge, a crown frame, a core material, the upper construction of an implant, an artificial tooth, various casts, experimental jigs, experimental structures; a jawbone-shaped cast used for artificial teeth, preoperative evaluation, and so on; directional/positioning jigs used when inserting implants; and so on. Furthermore, the structure is not limited to dental uses, and can be used as a structure aimed at obtaining a structure with an arbitrary form for use in other fields.

Embodiment 2

Embodiment 2 relates to a manufacturing method for manufacturing a structure such as a frame using the cross-sectional data 26 created by the modeling data creating system 1 of Embodiment 1 and the layered modeling apparatus 100. The layered modeling apparatus 100 is an apparatus that creates a desired model by layering, on a modeling table, modeling layers in which parts of the layers are selectively shaped.

Figure 17:
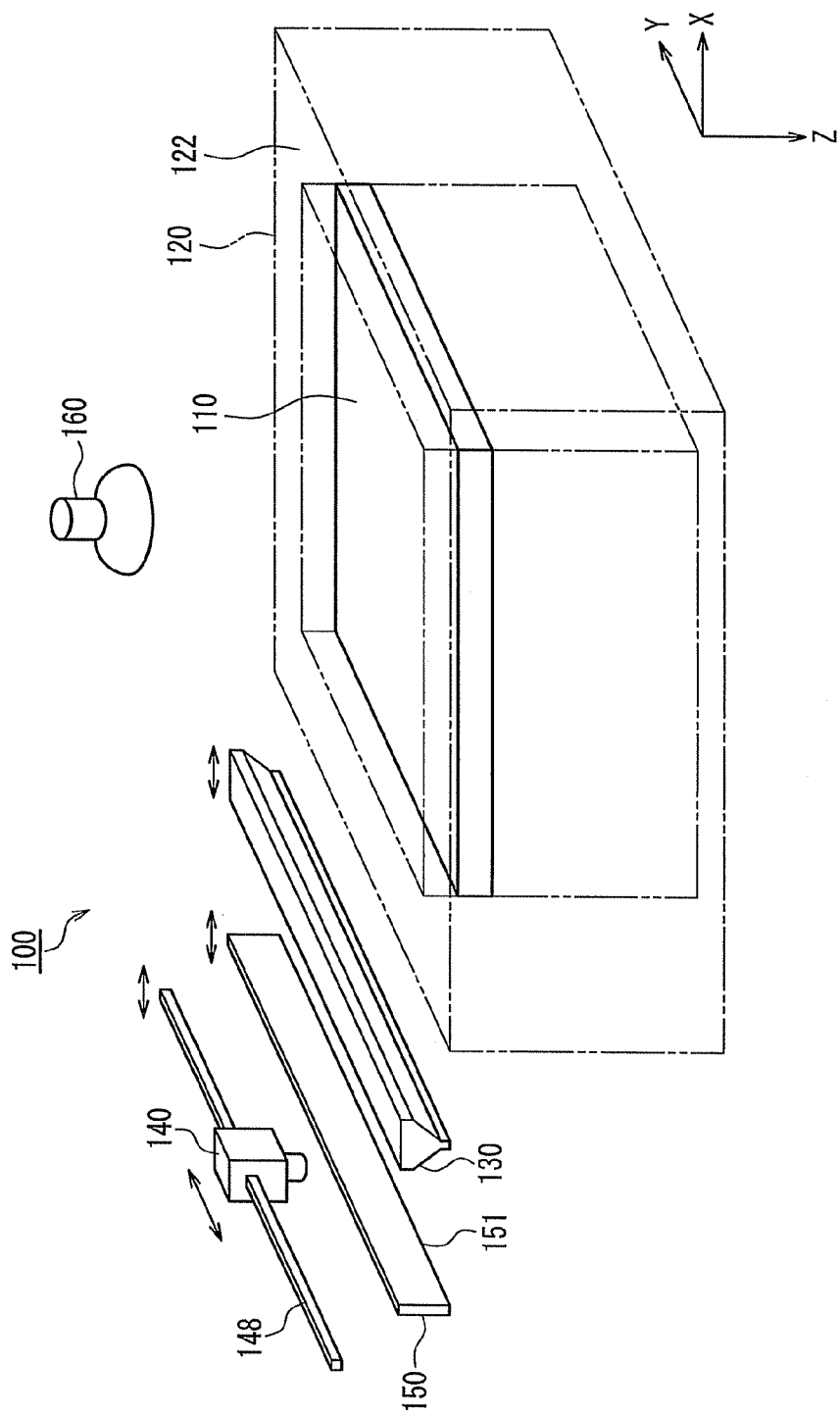
FIG. 17 is a perspective view illustrating the general configuration of a layered modeling apparatus 100.

FIG. 17 is a perspective view illustrating the general configuration of the layered modeling apparatus 100. In FIG. 17, the horizontal axes orthogonal to each other are taken as the X and Y axes, whereas the vertical axis is taken as the Z axis. As shown in FIG. 17, the layered modeling apparatus 100 includes a modeling table 110, a housing 120, a powder feeder 130, a solution feeder 140, a scraper member 150, and a light source 160. In FIG. 11, to make the construction easier to understand, the housing 120 is indicated by a double-dot-dash line, so that the modeling table 110 therein can be seen.

The modeling table 110 is capable of ascending/descending in the Z-axis direction. The housing 120 includes walls that encompass the perimeter of the modeling table 110 in the horizontal direction. The powder feeder 130 disperses a powder onto the modeling table 110. The solution feeder 140 ejects a solution onto the modeling table 110. The scraper member 150 smoothes the surface of the powder dispersed onto the modeling table 110 into a plane.

The light source 160 can be a light source for causing the photo-polymerization of the ejected solution, or can be a thermal light source for inducing the drying of the solution, as necessary.

The layered modeling apparatus 100 includes a computer (not shown). This computer controls the operations of the modeling table 110, the powder feeder 130, the solution feeder 140, the scraper member 150, and the light source 160 based on a predetermined control program.

The powder feeder 130 has a powder dispersal range of approximately the same width as the dimension of the modeling table 110 in the Y-axis direction. The powder feeder 130 disperses powder on the entire surface of the modeling table 110 by moving in the X-axis direction while dispersing powder.

The powder feeder 130 is moved in the X-axis direction by, for example, a slider (not shown). The computer can control the powder feeder 130 by sending control signals to a driver used to drive the slider.

The scraper member 150 has a scraping edge 151 that extends along its bottom end in the Y-axis direction. The scraper member 150 is moved in the X-axis direction while sliding the scraping edge 151 along the upper surface 122 of the housing 120. The scraper member 150 is moved in the X-axis direction by, for example, a slider (not shown).

The solution feeder 140 is, for example, an inkjet head. The solution feeder 140 moves along the Y-axis direction using a single-axis guide mechanism 148. This single-axis guide mechanism 148 is driven along the X-axis by a driving mechanism (not shown). In other words, the solution feeder 140 ejects the solution toward the modeling table 110 at predetermined positions while sweeping above the modeling table 110 in the X-axis and Y-axis directions. The layered modeling apparatus 100 may include, for example, a Y slider (not shown) that moves the solution feeder 140 in the Y-axis direction and an X slider (not shown) that moves the solution feeder 140 in the X-axis direction, provided in the single-axis guide mechanism 148.

The operation of the solution feeder 140 is controlled by the computer. The computer controls the solution feeder 140 by sending control signals to a driver for driving the X slider and the Y slider. In addition, the computer can control the positions at which the solution feeder 140 ejects the solution based on, for example, the cross-sectional data 26 generated by the modeling data creating system 1 and so on.

The modeling table 110 descends at a predetermined pitch using a driving mechanism (not shown). The pitch corresponds to the thickness of one layer of powder layered on the modeling table 110. In other words, the powder is layered on the modeling table 110 one thickness, which corresponds to the pitch, at a time. The modeling table 110 is moved in the vertical direction by, for example, a slider (not shown).

Next, a method by which the layered modeling apparatus 100 manufactures a model shall be described in detail using FIG. 18.

Figure 18A:
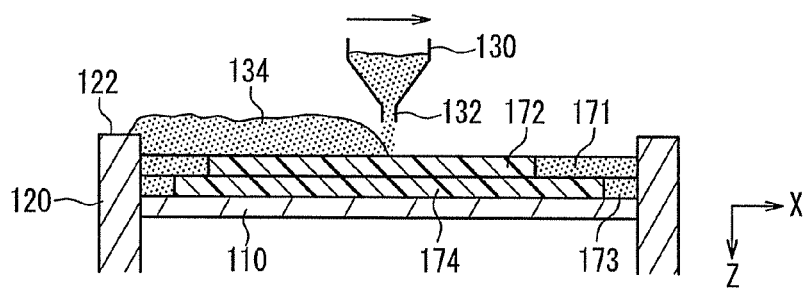
FIG. 18A is a cross-sectional view illustrating the first step in modeling performed by the layered modeling apparatus 100.

FIG. 18A illustrates a state in which multiple modeling layers (in FIG. 18A, two layers) created from powder have already been layered upon the modeling table 110. In the state shown in FIG. 18A, the uppermost layer 171 of the multiple modeling layers built up on the modeling table 110 includes a consolidated portion 172 formed through shaping by the solution. A modeling layer 173, formed immediately before the uppermost layer 171, also includes a consolidated portion 174 formed through shaping by the solution.

In the state shown in FIG. 18A, the powder feeder 130 disperses powder 134 from its slit 132 onto the modeling table 110 while moving in the X-axis direction.

Figure 18B:
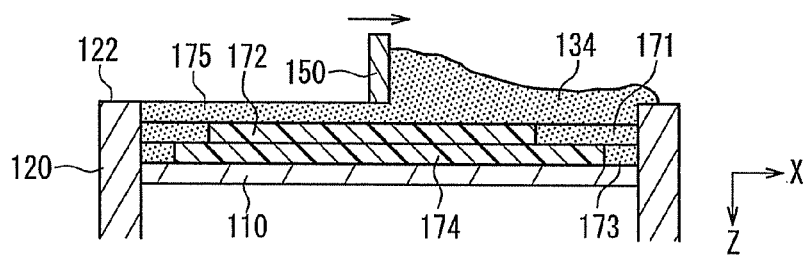
FIG. 18B is a cross-sectional view illustrating the next step in modeling performed by the layered modeling apparatus 100.

Next, as shown in FIG. 18B, the scraper member 150 moves in the X-axis direction, regulating the upper surface of the powder 134 to the same height as the upper surface 122 of the housing 120. Through this, a powder layer 175 having an even thickness is formed upon the uppermost layer 171.

Figure 18C:
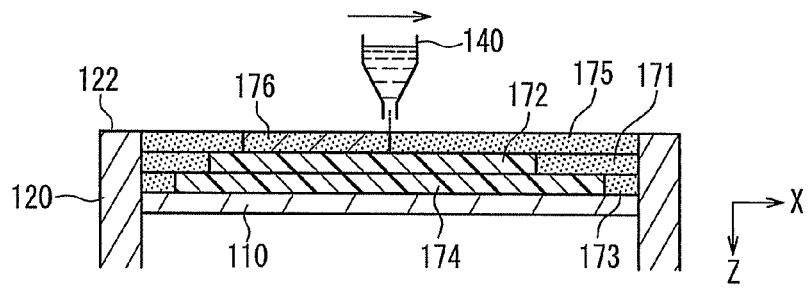
FIG. 18C is a cross-sectional view illustrating the next step thereafter in modeling performed by the layered modeling apparatus 100.

Next, as shown in FIG. 18C, the solution feeder 140 ejects the solution toward the positions in the powder layer 175 in which the model is to be formed, while moving. The positions at which the solution is ejected are controlled based on the cross-sectional data 26. For example, the solution feeder 140 ejects the solution so that the cross-sectional shape expressed by the cross-sectional data 26 is formed in the powder layer 175. As a result, the cross-sectional shape expressed by the cross-sectional data 26 is formed in the powder layer 175. In other words, the solution ejected by the solution feeder 140 acts as a binder liquid, saturating the powder layer 175 in the portions of the cross-sectional shape expressed by the cross-sectional data 26.

Figure 18D:
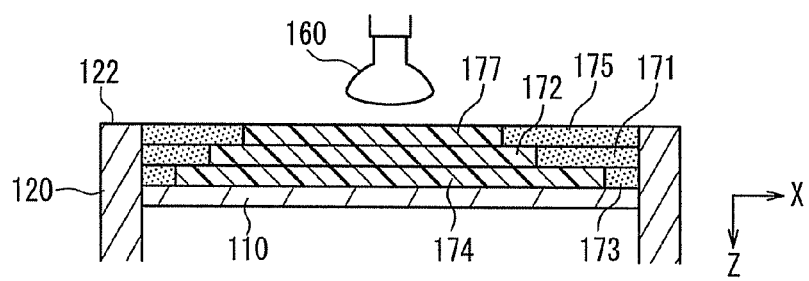
FIG. 18D is a cross-sectional view illustrating the next step thereafter in modeling performed by the layered modeling apparatus 100.

Next, as shown in FIG. 18D, the solution added to the powder layer 175 is polymerized and shaped through the irradiation of light by the light source 160. When the solution is shaped, the powder within the regions to which the solution was added coalesces into a single body. In this manner, a consolidated portion 177 is formed in the powder layer 175. The form of the consolidated portion 177 that has been formed is the same as the cross-sectional shape of a single cross-section expressed by the cross-sectional data 26.

Next, the modeling table 110 is caused to descend by a predetermined pitch, and the operations indicated in the stated FIGS. 18A to 18D are performed. The operations indicated in the stated FIGS. 18A to 18D are then repeated sequentially for each cross-section in the cross-sectional data 26.

Figure 18E:
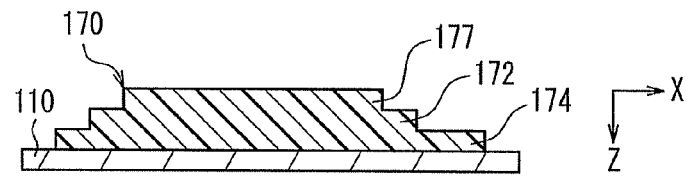
FIG. 18E is a cross-sectional view illustrating the next step thereafter in modeling performed by the layered modeling apparatus 100.

Finally, a model in which the consolidated portions 174, 172, and 177 are integrated, as shown in FIG. 18E, can be obtained by removing the unconsolidated powder from the modeling table 110. This model is then fired in, for example, a firing kiln.

A model in which the structure 31 and the support member 34 that supports the structure 31 are integrated can be manufactured by, for example, performing the abovementioned processes using the cross-sectional data 26 created by the modeling data creating system 1 of Embodiment 1.

Figure 19:
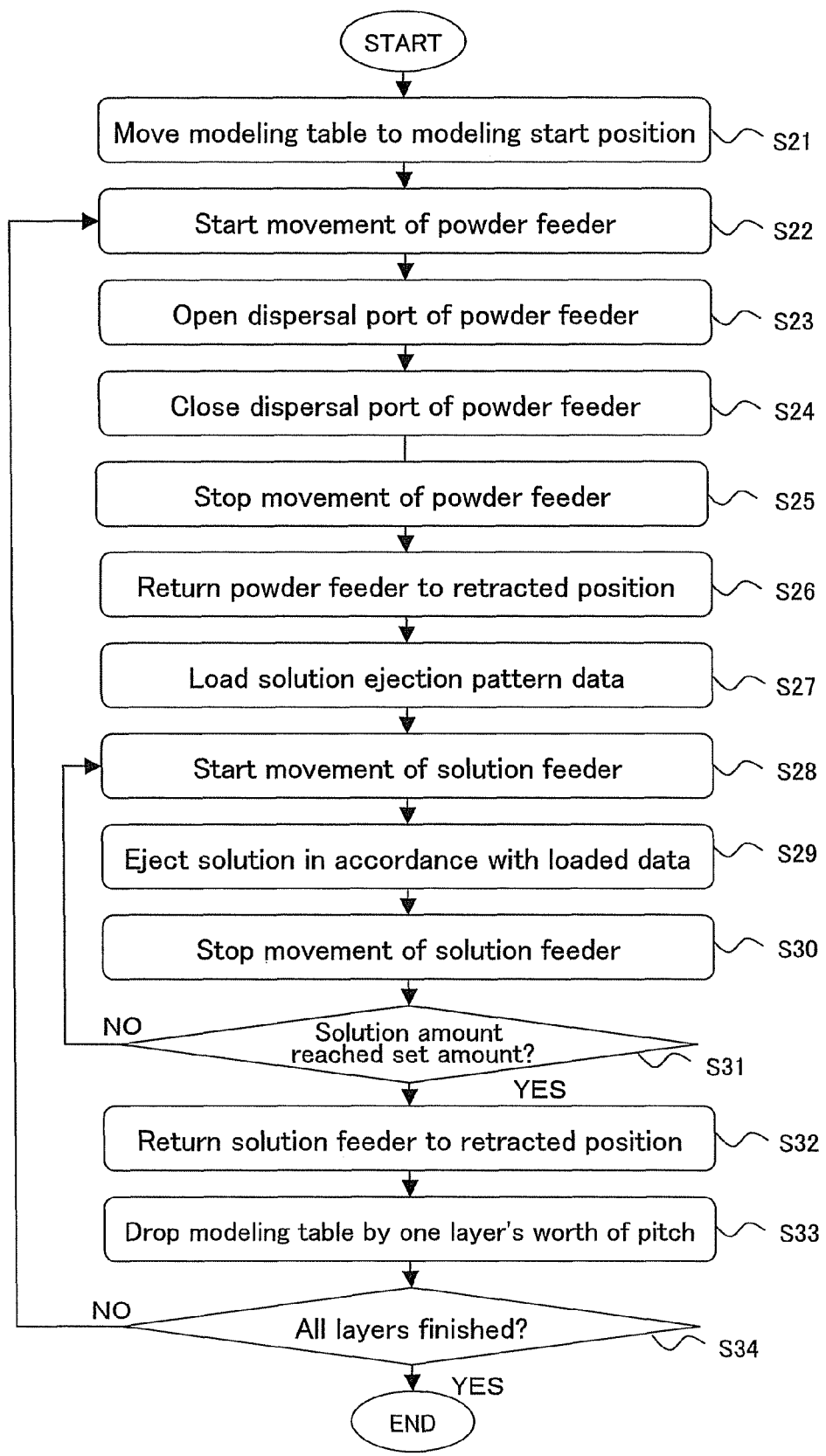
FIG. 19 is a flowchart illustrating an example of processes controlled by a control program.
Figure 20A:
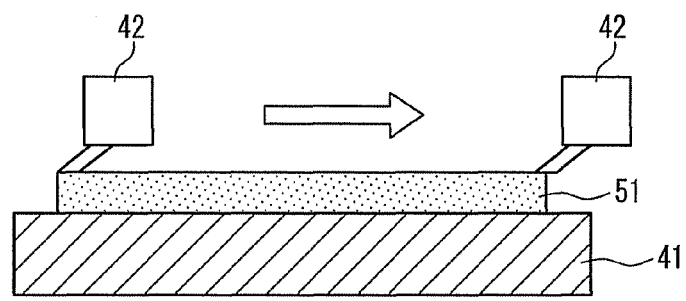
FIG. 20A is a diagram illustrating a step by which a conventional layered modeling apparatus forms a model.
Figure 20B:
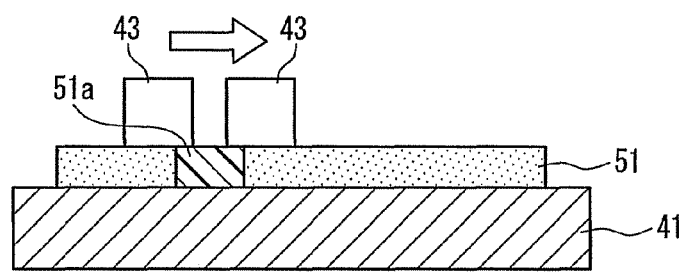
FIG. 20B is a diagram illustrating a step by which a conventional layered modeling apparatus forms a model.
Figure 20C:
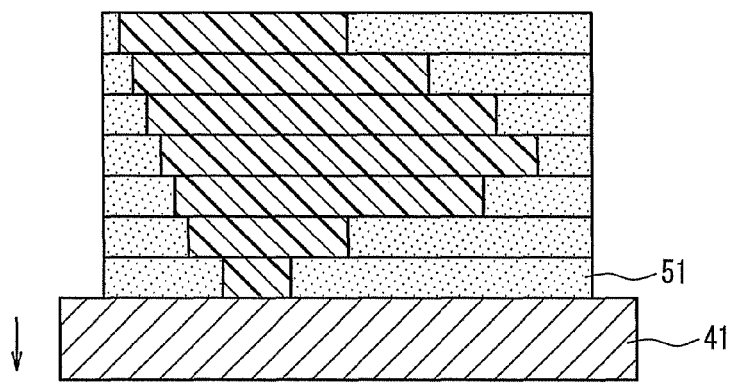
FIG. 20C is a diagram illustrating a step by which a conventional layered modeling apparatus forms a model.
Figure 20D:
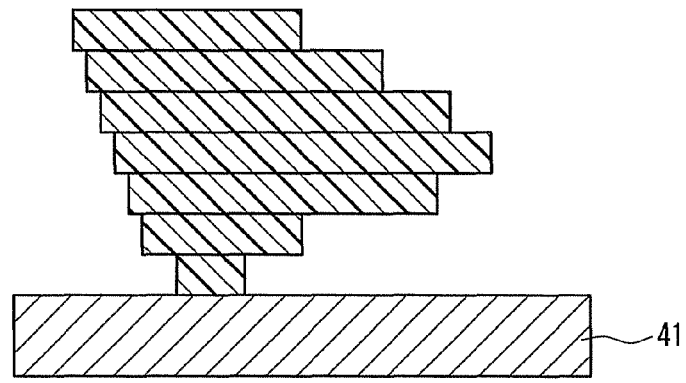
FIG. 20D is a diagram illustrating a step by which a conventional layered modeling apparatus forms a model.

The operations of the layered modeling apparatus 100 as described above can be executed by the computer provided in the layered modeling apparatus 100 controlling the layered modeling apparatus 100 based on a predetermined control program. Hereinafter, an example of control performed by a control program for implementing the operations shown in FIG. 18 shall be described. FIG. 19 is a flowchart illustrating an example of processes controlled by this control program.

First, the computer sends a control signal to the driver for driving the slider of the modeling table 110, thereby moving the modeling table 110 to a modeling start position (step S21). When the modeling table 110 is disposed in a predetermined position, the computer causes the powder feeder 130 to start to move (step S22). The computer can cause the powder feeder 130 to move by, for example, sending a control signal to a driver that drives the slider of the powder feeder 130.

After a set amount of time has elapsed following the start of movement of the powder feeder 130, the computer opens a dispersal port in the powder feeder 130 (step S23). The computer can determine that the powder feeder 130 has reached a constant speed and the acceleration thereof has dropped to zero following the passage of the set amount of time.

When the dispersal port of the powder feeder 130 has opened and the powder feeder 130 has moved a set distance after starting the dispersal of the powder 134 (or after a set amount of time has elapsed), the computer closes the dispersal port of the powder feeder 130 (step S24). After this, the computer stops the movement of the powder feeder 130 (step S25), and returns the powder feeder 130 to its retracted position (step S26).

Next, the computer loads data indicating a solution ejection pattern (step S27). The solution ejection pattern is, for example, the cross-sectional shape of a single cross section expressed by the cross-sectional data 26. The computer then causes the solution feeder 140 to start to move (step S28). When a set amount of time has elapsed following the start of movement, the computer determines that the solution feeder 140 has reached a constant speed and its acceleration has dropped to zero, and starts the ejection of the solution. The solution is ejected in accordance with the data loaded in step S27. When one cross-section's worth of solution has been ejected, the computer stops the movement the solution feeder 140 (step S30).

The computer then determines whether or not the amount of ejected solution has reached a pre-set amount (step S31). In the case where the amount of the solution has not reached the set amount (NO in step S31), the processes from step S28 to step S31 are executed again. In this manner, in the case where a large amount of solution is set, a predetermined amount of solution can be ejected by repeating steps S28 to S31 multiple times.

In the case of YES in step S31, the computer returns the solution feeder 140 to its retracted position (step S32), and drops the modeling table 110 by one layer's worth of pitch (step S33). The computer repeats the processes of steps S21 to 33 until the process is finished for all the layers (step S34). In other words, the processes of steps S21 to 33 are repeated the necessary number of times. The above has been an example of control performed by a control program for implementing the operations shown in FIG. 18.

In the process shown in FIG. 19, the data created by the modeling data creating system 1 in Embodiment 1 can be used as the cross-sectional data 26 loaded in step S27. A model in which the structure 31 and the support member 34 that supports the structure 31 are integrated is manufactured by using the data created by the modeling data creating system 1. The structure 31 is formed in a state in which it is supported by the support member 34, and thus is resistant to breakage during the formation process. In addition, the support member 34 can be removed from the structure 31 with ease, and has a form whereby remnants are unlikely to remain on the structure 31.

After the support member 34 has been removed, a step, of a thickness equivalent to one layer in the vertical direction, is present around the entire external surface. In addition, there are cases where fine serrations occur in the planar direction due to a combination of the resolution and ejection amount of the inkjet head and the particle size of the powder.

For example, in the case where the structure 31 is a frame, the surface thereof is not smooth. Accordingly, setting appropriate sintering conditions (firing conditions) in the firing process after the support member 34 has been removed makes it possible to eliminate steps in the surface of the model. In addition, by configuring the heating operations during the firing process of two processes, or a sintering/firing process and a glazing process, a sintered product or fired product with a glossy surface can be manufactured with precision.

Furthermore, if necessary, a post-processing (grinding, polishing, buffing) may be performed after the modeling. With the layered modeling apparatus 100, bridge frames formed using the cross-sectional data 26 created by the modeling data creating system 1 are resistant to breakage during the formation process, resistant to distortion during the sintering process, and unlikely to leave remnants when the support member 34 is removed. For this reason, the surface of the frame can be smoothed through post-processing with ease. Furthermore, it is highly likely that the precision at which the frame is fitted to the anchor tooth can be kept to a sufficient practical level.

Although Embodiment 2 discusses a method by which the layered modeling apparatus 100 manufactures a model by layering powder and then shaping a portion of each layer, the method for manufacturing a model through the layering of modeling layers is not limited to a method in which powder is layered. For example, an optical modeling method, in which a light-shapeable resin is layered and portions of the layers are shaped through light irradiation, or a method in which sheet material is layered and parts thereof are cut away can also be used. In addition, a powder sintering method, in which a layer of powder material is irradiated with a laser and the layer is shaped by flash-sintering part of the layer, may be used as well. An inkjet method, a resin extrusion method, a sheet shearing method, and so on are examples of other methods that can be used as the layered modeling method.

Finally, the configuration may be such that the modeling table 110 of the layered modeling apparatus 100 according to Embodiment 2 is provided with, for example, a rotational axis parallel to the table surface, enabling the table surface of the modeling table 110 to rotate in a manner that flips the table surface. An example of operations performed in the case where layered modeling is performed using such a rotatable modeling table 110 shall now be described. First, the solution is ejected onto the portions that are to be shaped, and then a layer of powder is dispersed. At this time, only the powder that has been dispersed on the portions where the solution was ejected makes contact with the solution and are shaped. After that, the modeling table is rotated so that the surface on which the powder was dispersed is flipped, and thus the powder that has not been shaped drops off under the force of gravity. Layered modeling is performed by repeating these operations.

The invention claimed is:

1. A modeling data creating system that creates modeling data expressing the form of a structure, the modeling data being used by a layered modeling apparatus that layers, upon a base plane, modeling layers that have been at least partially shaped through light irradiation or saturation of a binder liquid, the shaped parts forming the model, and the system comprising:
a structure data input unit that inputs structure data expressing the form of a desired structure;
a composition data recording unit that records composition data expressing the composition of a material used in the model formed by the layered modeling apparatus;
a change amount data recording unit that records the composition data of the material used in the model in association with the change amount data indicating the amount of change that the material will undergo due to drying, polymerization, or sintering;
a correction unit that obtains the composition data and the change amount data and corrects the structure data according to the change amount data so that the model formed using the corrected structure data resembles the form of the desired structure after the change caused by drying, polymerization, or sintering;
a contour generation unit that uses the corrected structure data to generate contour data expressing the contour of a space between the structure and a projection plane in which the structure is positioned above the base plane and the positioned structure is projected vertically onto the base plane;
a support member generation unit that generates support member data expressing the form of a support member that is formed so as to approximately fill the entirety of the space and support the structure; and
a cross-section generation unit that generates cross-sectional data expressing the cross-sectional shape of each of multiple planes approximately parallel to the base plane, based on the structure data, the support member data, and the contour data.

2. The modeling data creation system according to claim 1, wherein in the case where the desired structure is to be attached to another object, the structure data input unit further inputs relationship data indicating the relative positional relationship between the object and the structure; and
the system further comprises a supplementary form data generation unit that generates supplementary form data expressing a member for fixing the positional relationship between the object and the structure based on the relationship data, and adds the supplementary form data to the structure data.

3. The modeling data creating system according to claim 1, wherein the supplementary form data generation unit generates data expressing plate bodies or column bodies provided between the object and the structure as the supplementary form data, and generates the supplementary form data by finding the cross-sectional surface area of the plate bodies or column bodies using the composition data recorded in the composition data recording unit.

4. The modeling data creating system according to claim 2, wherein the supplementary form data generation unit generates the supplementary form data by calculating, using the structure data and the relationship data, the surface area of the portion where the member makes contact with the object so that the surface area is sufficient for fixing the positional relationship and sufficient for keeping the adhesive strength between the structure and the object above a predetermined value.

5. The modeling data creating system according to claim 2, wherein the supplementary form data generation unit generates supplementary form data expressing a member, formed from multiple plate bodies or column bodies, that is added to the surface of the structure indicated by the structure data that is attached to the object, that has a thickness equivalent to a desired space provided between the structure and the object, and whose surface that makes contact with the object is the same form as the form of the corresponding portion of the object.

6. The modeling data creating system according to claim 2, wherein the supplementary form data generation unit generates supplementary form data expressing a member formed from multiple plate bodies or column bodies extending in the normal direction in the portion of the structure that makes contact with the member.

7. The modeling data creating system according to claim 1, wherein the contour generation unit determines the positioning of the corrected structure based on the volume of a space formed between the corrected structure data corrected by the correction unit and the base plane, and generates contour data expressing the contour of the space formed between the corrected structure data and the base plane.

8. The modeling data creating system according to claim 1, where the support member data expresses a support member formed from multiple plate bodies or column bodies provided vertically relative to the base plane.

9. The modeling data creating system according to claim 8, wherein the support member data expresses a support member in which the horizontal thickness of the plate bodies or column bodies is, in the portion that makes contact with the structure, smaller than in the other portions.

10. The modeling data creating system according to claim 1, wherein the support member generation unit generates support member data expressing a support member having a notch near the portion that makes contact with the structure.

11. The modeling data creating system according to claim 1, wherein the support member generation unit corrects the structure data so that the periphery of the portion of the structure that makes contact with the support member is recessed toward the inner surface of the structure.

12. The modeling data creating system according to claim 8, wherein the composition data recording unit further records composition data expressing the composition of a material used in the support member; and
the support member generation unit finds the horizontal thickness of the plate bodies or column bodies using the composition data recorded in the composition data recording unit.

13. The modeling data creating system according to claim 1, wherein the support member generation unit calculates a distribution of force exerted on the support member by the structure using the structure data, and finds the horizontal thickness of the plate bodies or column bodies based on the distribution.

14. The modeling data creating system according to claim 1, wherein the structure is a prosthesis within the oral cavity, and the structure data is data generated based on measurement data obtained by measuring the interior of the oral cavity or the periphery thereof.

15. A manufacturing method for manufacturing the structure using the cross-sectional data created by the modeling data creating system according to claim 1 and the layered modeling apparatus, the method comprising:
a layer formation step of forming a modeling layer of a predetermined thickness upon a modeling table, provided in the layered modeling apparatus, that is capable of moving up and down;
a modeling step of selectively irradiating with light or ejecting a binder liquid onto and saturating at least a portion of the modeling layer, the portion having a form corresponding to a cross-sectional shape expressed by the cross-sectional data, thereby shaping the modeling layer;
a descent step of causing the modeling table to descend by an amount equivalent to the predetermined thickness;
a layering step of layering modeling layers by sequentially repeating the layer formation step and the shaping step for each of multiple planes expressed by the cross-sectional data; and
a removal step of forming the structure in a state in which the structure is supported upon the modeling table by the support member, by removing the portions of the modeling layer layered in the layering step aside from the portions shaped in the shaping step.

16. A modeling data creating program that causes a computer to execute a process for creating modeling data expressing the form of a structure, the modeling data being used by a layered modeling apparatus that layers, upon a base plane, modeling layers that have been at least partially shaped through light irradiation or saturation of a binder liquid, the shaped parts forming the model, and the program comprising:
a structure data input process of inputting structure data expressing the form of a desired structure;
a correction process of accessing a composition data recording unit that records composition data expressing the composition of the material used in the model formed by the layered modeling apparatus and a change amount data recording unit that records the composition data in association with change amount data indicating the amount of change that the material will undergo due to drying, polymerization, or sintering, obtaining the change amount data and the composition data and, based on the obtained change amount data, correcting the structure data so that the model formed using the structure data resembles the form of the corrected structure after the change caused by drying, polymerization, or sintering;
a contour generation process of using the structure data to generate contour data expressing the contour of the space between the structure and a projection plane in which the structure is positioned above the base plane and the positioned structure is projected vertically onto the base plane;
a support member generation process of generating support member data expressing the form of a support member that is formed so as to approximately fill the entirety of the space and support the structure; and
a cross-section generation process of generating, based on the structure data, the support member data, and the contour data, cross-sectional data expressing the cross-sectional shape of each of multiple planes approximately parallel to the base plane, the planes making up the model configured of the support member expressed by the support member data and the structure expressed by the structure data corrected by the correction unit.

17. The modeling data creating system according to claim 3, wherein the supplementary form data generation unit generates supplementary form data expressing a member, formed from multiple plate bodies or column bodies, that is added to the surface of the structure indicated by the structure data that is attached to the object, that has a thickness equivalent to a desired space provided between the structure and the object, and whose surface that makes contact with the object is the same form as the form of the corresponding portion of the object.

18. The modeling data creating system according to claim 3, wherein the supplementary form data generation unit generates supplementary form data expressing a member formed from multiple plate bodies or column bodies extending in the normal direction in the portion of the structure that makes contact with the member.

* * * * *